United States Patent
Hausmann et al.

(10) Patent No.: US 9,163,237 B2
(45) Date of Patent: *Oct. 20, 2015

(54) REPLICATION DEFICIENT RECOMBINANT VIRUSES EXPRESSING ANTIGENS REGULATED BY TRANSCRIPTIONAL CONTROL ELEMENTS COMPRISING MULTIPLE ELEMENTS

(71) Applicant: Bavarian Nordic A/S, Kvistgaard (DK)

(72) Inventors: Jürgen Hausmann, Gundelfingen (DE); Karen Baur, Munich (DE); Kay Brinkmann, Munich (DE)

(73) Assignee: BAVARIAN NORDIC A/S, Kvistgaard (DK)

( * ) Notice: Subject to any disclaimer, the term of this patent is extended or adjusted under 35 U.S.C. 154(b) by 43 days.

This patent is subject to a terminal disclaimer.

(21) Appl. No.: 14/096,916

(22) Filed: Dec. 4, 2013

(65) Prior Publication Data

US 2014/0113368 A1   Apr. 24, 2014

Related U.S. Application Data

(60) Division of application No. 13/220,771, filed on Aug. 30, 2011, now Pat. No. 8,613,936, which is a continuation-in-part of application No. PCT/EP2010/001545, filed on Mar. 11, 2010, said application No. 13/220,771 is a continuation-in-part of application No. 12/719,987, filed on Mar. 9, 2010, now Pat. No. 8,394,385.

(60) Provisional application No. 61/159,857, filed on Mar. 13, 2009.

(30) Foreign Application Priority Data

Jul. 28, 2009   (EP) ..................... 09009759

(51) Int. Cl.
| | |
|---|---|
| C12N 15/113 | (2010.01) |
| A61K 39/285 | (2006.01) |
| C07K 14/005 | (2006.01) |
| C12N 15/86 | (2006.01) |
| A61K 39/12 | (2006.01) |

(52) U.S. Cl.
CPC .............. *C12N 15/113* (2013.01); *A61K 39/12* (2013.01); *A61K 39/285* (2013.01); *C07K 14/005* (2013.01); *C12N 15/86* (2013.01); *C12N 2710/24122* (2013.01); *C12N 2710/24134* (2013.01); *C12N 2710/24143* (2013.01)

(58) Field of Classification Search
None
See application file for complete search history.

(56) References Cited

U.S. PATENT DOCUMENTS

| | | | | |
|---|---|---|---|---|
| 6,001,369 A | * | 12/1999 | Cochran et al. | ............. 424/199.1 |
| 6,761,893 B2 | | 7/2004 | Chaplin et al. | |
| 8,394,385 B2 | | 3/2013 | Hausmann et al. | |
| 2003/0166251 A1 | * | 9/2003 | Kim et al. | .................. 435/235.1 |
| 2010/0233203 A1 | | 9/2010 | Hausmann et al. | |
| 2012/0014988 A1 | | 1/2012 | Hausmann et al. | |

FOREIGN PATENT DOCUMENTS

| | | |
|---|---|---|
| CA | 2104649 A1 | 2/1994 |
| EP | 1536015 A1 | 6/2005 |
| WO | 02/42480 A2 | 5/2002 |
| WO | 2010/102822 A1 | 9/2010 |

OTHER PUBLICATIONS

Assarsson et al., Kinetic analysis of a complete poxvirus transcriptome reveals an immediate-early class of genes, Proc. Natl. Acad. Sci. 105:2140-2145 (2008).
Bronte et al., Antigen expression by dendritic cells correlates with the therapeutic effectiveness of a model recombinant poxvirus tumor vaccine, Proc. Natl. Acad. Sci. 94:3183-3188 (1997).
Broyles, Vaccinia virus transcription, Journal of General Virology 84:2293-2303 (2003).
Carroll et al., Host Range and Cytopathogenicity of the Highly Attenuated MVA Strain of Vaccinia Virus: Propagation and Generation of Recombinant Viruses in a Nonhuman Mammalian Cell Line, Virology 238:198-211 (1997).
Chakrabarti et al., Compact, Synthetic, Vaccinia Virus Early/Late Promoter for Protein Expression, BioTechniques 23:1094-1097 (Dec. 1997).
Cochran et al., In Vitro Mutagenesis of the Promoter Region for a Vaccinia Virus Gene: Evidence for Tandem Early and Late Regulatory Signals, Journal of Virology 54:30-37 (1985).
Cosma et al., Therapeutic vaccination with MVA-HIV-1 nef elicits Nef-specific T-helper cell responses in chronically HIV-1 infected individuals, Vaccine 22:21-29 (2003).
Coupar et al., Temporal regulation of influenza hemagglutinin expression in vaccinia virus recombinants and effects on the immune response, Eur. J. Immunol. 16: 1479-1487 (1986).
Davison et al., Structure of Vaccinia Virus Early Promoters, J. Mol. Biol. 210:749-769 (1989).
Davison et al., Structure of Vaccinia Virus Late Promoters, J. Mol. Biol. 210:771-784 (1989).
Di Nicola et al., Immunization of Patients with Malignant Melanoma with Autologous CD341 Cell-Derived Dendritic Cells Transduced Ex Vivo with a Recombinant Replication-Deficient Vaccinia Vector Encoding the Human Tyrosinase Gene: A Phase I Trial, Human Gene Therapy 14:1347-1360 (Sep. 20, 2003).

(Continued)

*Primary Examiner* — Louise W Humphrey
(74) *Attorney, Agent, or Firm* — Law Office of Salvatore Arrigo and Scott Lee, LLP

(57) ABSTRACT

The present invention relates to a replication deficient recombinant virus encoding at least one antigen and/or antigenic epitope, wherein expression of said antigen and/or antigenic epitope is regulated by a transcriptional control element comprising at least two elements driving early expression of said antigen and/or antigenic epitope and the use of said replication deficient recombinant virus as medicament or vaccine.

11 Claims, 6 Drawing Sheets

(56) References Cited

OTHER PUBLICATIONS

Di Nicola et al., Boosting T Cell-Mediated Immunity to Tyrosinase by Vaccinia Virus-Transduced, CD34+-Derived Dendritic Cell Vaccination: A Phase I Trial in Metastatic Melanoma, Clinical Cancer Research 10:5381-5390 (2004).

Funahashi et al., Increased Expression In Vivo and In Vitro of Foreign Genes Directed by A-Type Inclusion Body Hybrid Promoters in Recombinant Vaccinia Viruses, Journal of Virology 65:5584-5588 (1991).

Harrer et al., Therapeutic Vaccination of HIV-1-infected patients on HAART with a recombinant HIV-1 nef-expressing MVA:safety, immunogenicity and influence on viral load during treatment, Antivaral Therapy 10:285-300 (2005).

Hirschmann et al., Mutational Analysis of a Vaccinia Virus Intermediate Promoter In Vivo and In Vitro, Journal of Virology 64:6063-6069 (1990).

Jin et al., Construction of a vaccinia viruss A-type inclusion body protein, tandemly repeated mutant 7.5 kDA protein, and hemagglutinin gene promoters support high levels of expression, Arch Virol 138:315-330 (1994).

Kastenmuller et al., Cross-competition of CD8 + T cells shapes the immunodominance hierarchy during boost vaccination, J. Exp. Med. 204:2187-2198 (2007).

Patel et al., A poxvirus-derived vector that directs high levels of expression of cloned genes in mammalian cells, Proc. Natl. Acad. Sci. 85:9431-9435 (1988).

Smith et al., Immunodominance of Poxviral-Specific CTL in a Human Trial of Recombinant-Modified Vaccinia Ankara, Journal of Immunology 175: 8431-8437 (2005).

Sutter et al., Nonreplicating vaccinia vector efficiently expresses recombinant genes, Proc. Natl. Acad. Sci. 89:10847-10851 (1992).

Tscharke et al., Identification of poxvirus CD8+ T cell determinants to enable rational design and characterization of smallpox vaccines, J. Exp. Med. 201:95-104 (2004).

Wyatt et al., Correlation of immunogenicities and in vitro expression levels of recombinant modified vaccinia virus Ankara HIV vaccines, Vaccine 26:486-493 (2008).

Rosel et al., Conserved TAAATG Sequence at the Transcriptional and Translational Initiation Sites of Vaccinia Virus Late Genes Deduced by Structural and Functional Analysis of the HindIII H Genome Fragment, Journal of Virology, 60:436-449 (1986).

Mayrhofer et al., Nonreplicating Vaccinia Virus Vectors Expressing the H5 Influenza Virus Hemagglutinin Produced in Modified Vero Cells Induce Robust Protection, J. Virol 83 (10): 5192-5203 (2009).

Boyle et al., Quantative Assessment of Poxvirus Promoters in Fowlpox and Vacinnia Virus Recombinants, Virus Genes 6(3): 281-290 (1992).

* cited by examiner

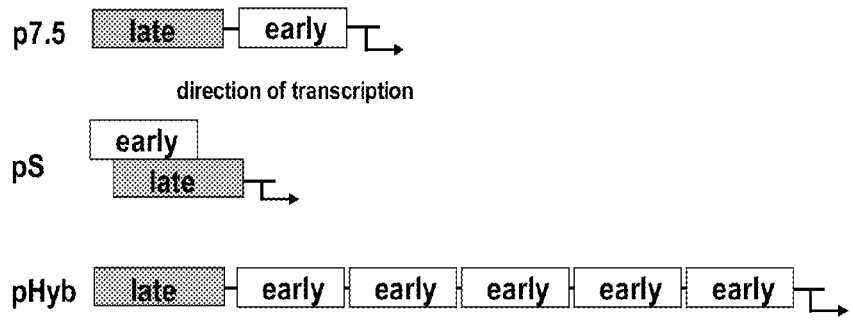

A p7.5 [late]—[early]⊥→ direction of transcription pS [early / late]⊥→ pHyb [late]—[early | early | early | early | early]⊥→

B p7.5  5´tccaaacccacccgcttttttatagtaagttttt
cacccataaataataaatacaataattaatttctc
gtaaaagtagaaaatatattctaatttattgcacgg 3´ aaaaattgaaaaacta = optimized portion of p7.5 early element pS  5´aaaaattgaaattttatttttttttttggaatataaata 3´ pHyb 5´acgcgtgtttaaacgttttgaaaatttttttataataaata
tccggtaaaaattgaaaaactattctaatttattgcacggtcc
ggtaaaaattgaaaaactattctaatttattgcacggtccggt
aaaaattgaaaaactattctaatttattgcacggtccggt
aaaaattgaaaaactattctaatttattgcacggtccggt
aaaaattgaaaaactattctaatttattgcacggtccgga 3´

REPLICATION DEFICIENT RECOMBINANT VIRUSES EXPRESSING ANTIGENS REGULATED BY TRANSCRIPTIONAL CONTROL ELEMENTS COMPRISING MULTIPLE ELEMENTS

CROSS-REFERENCE TO RELATED APPLICATIONS

This application is a divisional of U.S. application Ser. No. 13/220,771, filed Aug. 30, 2011, which is a continuation-in-part of International Appln. PCT/EP2010/001545, filed Mar. 11, 2010, which claims the benefit of U.S. Provisional Application No. 61/159,857, filed Mar. 13, 2009, and EP Appln. No. 09009759.3 filed Jul. 28, 2009. U.S. application Ser. No. 13/220,771 is also a continuation-in-part of U.S. application Ser. No. 12/719,987, filed Mar. 9, 2010, now U.S. Pat. No. 8,394,385, which claims the benefit of U.S. Provisional Application No. 61/159,857, filed Mar. 13, 2009, and EP Appln. No. 09009759.3 filed Jul. 28, 2009. All of the above applications are incorporated herein by reference.

FIELD OF THE INVENTION

The present invention relates to a replication deficient recombinant virus encoding at least one antigen and/or antigenic epitope, wherein expression of said antigen and/or antigenic epitope is regulated by a transcriptional control element comprising at least two elements driving early expression of said antigen and/or antigenic epitope and the use of said replication deficient recombinant virus as medicament or vaccine.

BACKGROUND OF THE INVENTION

Live attenuated, replicating vaccines, rather than inactivated preparations, have provided the most effective protection against viral infection and disease. These vaccines elicit essentially life-long protective immunity. In contrast, immunity induced by inactivated or subunit vaccines is generally of more limited duration. A key factor in pursuit of the latter approaches is safety. An overview of replicating and non-replicating viral vectors for vaccine development is given in the publication of Marjorie Robert-Guroff, Replicating and Non-replicating Viral Vectors for Vaccine Development, Curr. Opin. Biotechnol. 18:546-556, 2007.

Recombinant viruses are widely used to express foreign antigens in infected cells. Specifically, recombinant poxviruses are currently tested as promising vaccines to induce an immune response against a foreign antigen expressed from the poxvirus vector. Most popular are avipoxviruses on the one side and vaccinia viruses (VACV) on the other side. U.S. Pat. No. 5,736,368 and U.S. Pat. No. 6,051,410 disclose recombinant vaccinia virus strain Wyeth which expresses HIV antigens and proteins. U.S. Pat. No. 5,747,324 discloses a recombinant VACV strain NYCBH expressing lentivirus genes. EP 0 243 029 discloses a recombinant VACV strain Western Reserve expressing human retrovirus genes. For the expression of heterologous genes in poxviruses several promoters are known to the person skilled in the art, such as the 30K and 40K promoters (see, e.g., U.S. Pat. No. 5,747,324), a strong synthetic early/late promoter (see, e.g., Sutter et al., A recombinant vector derived from the host range-restricted and highly attenuated MVA strain of vaccinia virus stimulates protective immunity in mice to influenza virus, Vaccine 12, 1032-40, 1994), the p7.5 promoter (see, e.g., Endo et al., Homotypic and heterotypic protection against influenza virus infection in mice by recombinant vaccinia virus expressing the haemagglutinin or nucleoprotein of influenza virus, J. Gen. Virol. 72, 699-703, 1991) and the promoter derived from the cowpox virus A-type inclusion (ATI) gene (Li et al., High-level expression of Amsacta moorei entomopoxvirus spheroidin depends on sequences within the gene, J. Gen. Virol. 79, 613, 1998). All of these promoters have been used in recombinant VACV to express heterologous genes and were shown to express said genes very efficiently resulting in relatively high amounts of the protein encoded by the heterologous gene. In general, for many vaccination approaches it is highly desired that the antigen against which an immune response is to be induced is expressed in high amounts.

Induction of a strong humoral and cellular immune response against a foreign gene product expressed by, e.g., a VACV vector is hampered by the fact that the foreign gene product has to compete with all of the more than 150 antigens of the VACV vector for recognition and induction of specific antibodies and T cells. Immunodominance of vector CD8 T cell epitopes prevents induction of a strong CD8 T cell response against the foreign gene product. (Smith et al., Immunodominance of poxviral-specific CTL in a human trial of recombinant-modified vaccinia Ankara. J. Immunol. 175: 8431-8437, 2005.) This applies to replicating VACV vectors such as Dryvax, as well as to replication deficient vectors like NYVAC and Modified Vaccinia virus Ankara, MVA.

For expression of a recombinant antigen by VACV poxvirus-specific promoters but not common eukaryotic promoters may be used. The reason for this is the specific biology of poxviruses which replicate in the cytoplasm and bring their own, cell-autonomous transcriptional machinery with them that does not recognize typical eukaryotic promoters.

The viral replication cycle is divided into two major phases, an early phase comprising the first two hours after infection before DNA replication, and a late phase starting at the onset of viral DNA replication at 2-4 hours after infection. The late phase spans the rest of the viral replication cycle from ~2-20 h after infection until progeny virus is released from the infected cell. There are a number of poxviral promoter types which are distinguished and named by the time periods within the viral replication cycle in which they are active, for example, early and late promoters. (See, e.g., Davison and Moss, Structure of Vaccinia Virus Late Promoters, J. Mol. Biol. 210:771-784, 1989; Davison and Moss, Structure of Vaccinia Virus Early Promoters, J. Mol. Biol. 210:749-769, 1989; and Hirschmann et al., Mutational Analysis of a Vaccinia Virus Intermediate Promoter in vitro and in vivo, Journal of Virology 64:6063-6069, 1990, all of which are hereby incorporated by reference.)

Whereas early promoters can also be active late in infection, activity of late promoters is confined to the late phase. A third class of promoters, named intermediate promoters, is active at the transition of early to late phase and is dependent on viral DNA replication. The latter also applies to late promoters, however, transcription from intermediate promoters starts earlier than from typical late promoters and requires a different set of transcription factors.

It became increasingly clear over recent years that the choice of the temporal class of poxviral promoter for antigen expression has profound effects on the strength and quality of the antigen-specific immune response. It was shown that T cell responses against antigens expressed under the control of a late promoter are weaker than those obtained with the same antigen under the control of an early promoter. (Bronte et al., Antigen expression by dendritic cells correlates with the therapeutic effectiveness of a model recombinant poxvirus tumor vaccine. Proc. Natl. Acad. Sci. U.S.A 94:3183-3188, 1997; Coupar et al., Temporal regulation of influenza hemagglutinin expression in vaccinia virus recombinants and effects on the immune response. Eur. J. Immunol. 16:1479-1487, 1986.)

Even more strikingly, it was shown that in repeated autologous immunizations with VACV as well as with the replication-defective VACV vector MVA, recall CD8 T cell responses against antigens under the control of an exclusively late promoter can fail completely. This failure resulted in an almost undetectable antigen-specific CD8 T cell response after the second immunization (Kastenmuller et al., Cross-competition of CD8+ T cells shapes the immunodominance hierarchy during boost vaccination. J. Exp. Med. 204:2187-2198, 2007.)

Thus, early expression of antigens by VACV vectors appears to be crucial for efficient antigen-specific CD8 T cell responses. It has also been shown that an early-expressed VACV vector antigen not only competes with late expressed antigens but also with other early antigens for immunodominance in the CD8 T cell response (Kastenmuller et al., Cross-competition of CD8+ T cells shapes the immunodominance hierarchy during boost vaccination., J. Exp. Med. 204:2187-2198, 2007). The specific properties of the early portion of the poxviral promoter might thus be important for induction of an antigen-specific T cell response. Moreover, it is a commonly held view and a general rule that higher amounts of antigen are beneficial for induction of stronger antigen-specific immune responses (for the poxvirus field, see for example Wyatt et al., Correlation of immunogenicities and in vitro expression levels of recombinant modified vaccinia virus Ankara HIV vaccines. Vaccine 26:486-493, 2008.)

A promoter combining 4 early promoter elements and a late promoter element from the ATI gene has been described previously and has been shown to direct increased early antigen expression (Funahashi et al., Increased expression in vivo and in vitro of foreign genes directed by A-type inclusion body hybrid promoters in recombinant vaccinia viruses. J. Virol. 65:5584-5588, 1991; Wyatt et al., Correlation of immunogenicities and in vitro expression levels of recombinant modified vaccinia virus Ankara HIV vaccines. Vaccine 26:486-493, 2008). T cell responses induced by an antigen driven by such a promoter in a recombinant replication competent vaccinia virus vector have been analyzed after a single immunization and were, however, found to be only slightly different from those obtained with the classical p7.5 promoter in this setting. (Funahashi et al., 1991.)

Jin et al. (Constructions of vaccinia virus A-type inclusion body protein, tandemly repeated mutant 7.5 kDa protein, and hemagglutinin gene promoters support high levels of expression, Arch. Virol. 138:315-330, 1994) reported the construction of recombinant VACV harbouring promoters consisting of a VACV ATI promoter combined with tandem repeats (2 to 38 copies) of a mutated p7.5 promoter operably linked to the CAT gene. Up to 10-15 repetitions of the mutated p7.5 promoter appeared to be effective in increasing early gene expression. However, with all constructs, the amount of CAT protein produced in the presence of cytosine arabinoside (AraC) (i.e. when the viral replication cycle was arrested in the early phase) was only less than one-tenth of the amount produced in the absence of AraC, indicating that although early gene expression was increased, most of the expressed antigen was obviously produced during the late phase of infection.

Accordingly, there is a need for improved viral vectors that enable early expression of foreign antigens and induction of a strong antigen-specific immune response.

SUMMARY OF THE INVENTION

The present invention relates to a replication deficient recombinant virus encoding at least one antigen and/or antigenic epitope, wherein expression of said antigen and/or antigenic epitope is regulated by a transcriptional control element comprising at least two elements driving early expression of said antigen and/or antigenic epitope.

The invention further relates to said replication deficient recombinant virus for use as medicament or vaccine and its use for the preparation of a medicament or vaccine.

In another aspect the present invention relates to a pharmaceutical composition or vaccine comprising the replication deficient recombinant virus and, optionally, a pharmaceutically acceptable carrier, diluent, adjuvant and/or additive.

The invention also relates to said replication deficient recombinant virus or said pharmaceutical composition or vaccine for inducing a T cell response in a host to said at least one antigen and/or antigenic epitope.

In a further aspect it relates to the use of said replication deficient recombinant virus or said pharmaceutical composition or vaccine for the preparation of a medicament for inducing a T cell response in a host to said at least one antigen and/or antigenic epitope.

The invention also encompasses a kit comprising at least two vials for prime/boost immunization comprising said replication deficient recombinant virus for a first inoculation ("priming inoculation") in a first vial/container and for an at least second and/or third and/or further inoculation ("boosting inoculation") in a second and/or further vial/container.

The invention further relates to a method of inducing a T cell response, preferably a CD8 T cell response, in a host, including a human, said method comprising a least three or at least four administrations of the replication deficient recombinant virus to the host.

Also encompassed by the present invention is a promoter comprising at least 2 nucleotide sequence elements according to nt 48-81 of SEQ ID NO:1 and/or at least 2 nucleotide sequence elements having at least 80% identity to nt 48-81 of SEQ ID NO:1.

BRIEF DESCRIPTION OF THE FIGURES

FIGS. 1A and B depict sequence and schematic representation of the arrangement of early and late promoter elements in pHyb, p7.5 and pS. A) Schematic representation of p7.5, pS and pHyb promoters. Early and late promoter elements are not drawn to scale. B) Nucleotide sequence of the p7.5 (SEQ ID NO:5), pS (SEQ ID NO:2) and pHyb (SEQ ID NO:1) promoters. The region where the p7.5 early promoter element has been optimized is boxed in the p7.5 sequence and the optimized sequence is shown below. Single solid line: late promoter element. Double line: early promoter element.

DETAILED DESCRIPTION OF THE INVENTION

Figure 2:
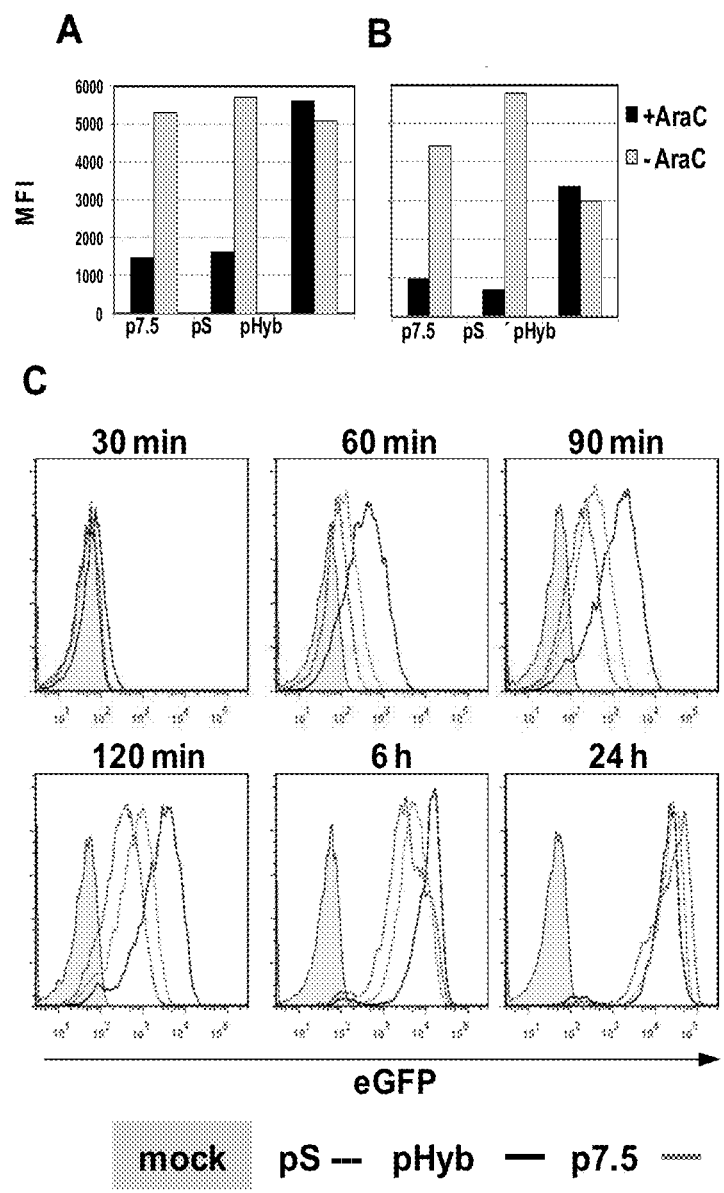
FIGS. 2 A-D depict expression of eGFP directed by recombinant MVAs. Recombinant MVAs containing the eGFP open reading frame under control of the indicated promoters were used to infect HeLa (A, C), CEF cells (B), and EL4 cells (D) at a multiplicity of infection (MOI or m.o.i.) of 5 (A-C) or 10 (D). Cells were either treated with cytosine arabinoside (+AraC) or were left untreated (−AraC) during infection (A, B). Cells were harvested 16 h p.i. (A, B) and analyzed by flow cytometry for eGFP expression. C) HeLa cells were infected with MVA-p7.5-eGFP ("p7.5"), MVA-pS-eGFP ("pS"), and MVA-pHyb-eGFP ("pHyb"), or incubated with medium ("Mock"). At the indicated times after infection, cells were harvested and analyzed by flow cytometry for eGFP expression. The experiments were independently repeated at least two times. D) Murine EL-4 cells were infected at an MOI of 10 with MVA vector alone (filled grey), MVA-pHyb-OVA ("pHyb"), MVA-p7.5-OVA ("p7.5"), or MVA-pS-OVA ("pS"). At the indicated times after infection, cells were collected in ice-cold PBS+2% FCS and complexes of OVA-derived peptide SIINFEKL and MHC class I molecules were stained with an antibody (clone 25D1.16) specific for SIINFEKL bound to the murine MHC 1 molecule H-2 Kb. Stained cells were analyzed by flow cytometry. pOVA:MHC I=SIINFEKL/H-2 Kb complex.
Figure 2:
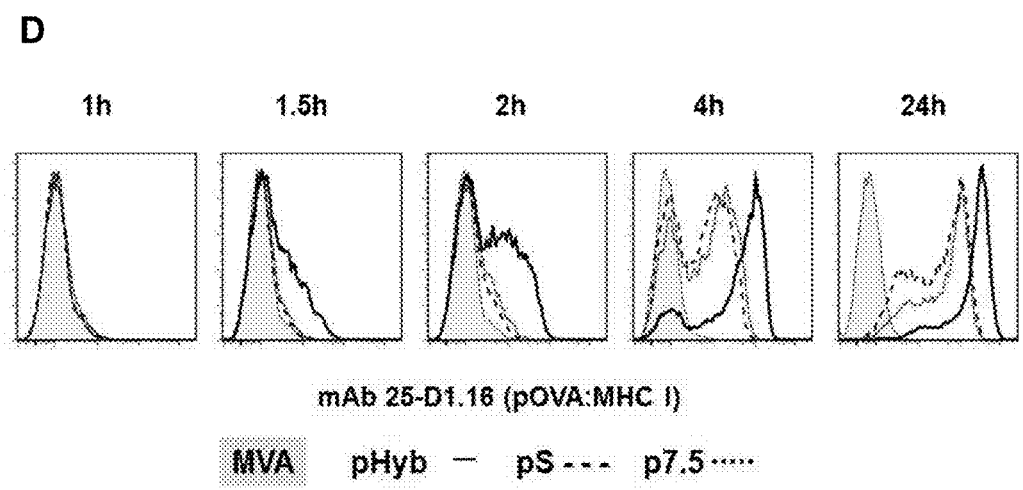

The present invention relates to a replication deficient recombinant virus encoding at least one antigen and/or antigenic epitope, wherein expression of said antigen and/or antigenic epitope is regulated by a transcriptional control element comprising at least two elements driving early expression of said antigen and/or antigenic epitope.

It was surprisingly found that with replication deficient recombinant viruses the expression of an antigen regulated by a transcriptional control element comprising at least two elements driving early expression occurred significantly earlier in the viral replication cycle and was also significantly higher at earlier timepoints after infection than expression driven by a conventional transcriptional control element. Additionally, the advantage in strong early antigen expression even persists until at least 6 h after infection.

Accordingly, in a preferred embodiment of the present invention, the at least two elements drive immediate early expression of the antigen and/or antigenic epitope, i.e. within the first hour after infection, preferably within the first 30 minutes after infection.

The ability of a very early expressed antigen under control of the transcriptional control element according to the invention to outcompete vector-derived early antigens during recall responses was investigated by administering the replication deficient recombinant virus and subsequent determination of T cell responses. Immunization unexpectedly resulted in highly efficient antigen-specific T cell responses, in particular in CD8 T cell responses. Even more surprising, in some of the experiments, this approach was even able to reverse immunodominance hierarchy and convert a subdominant CD8 T cell epitope into the immunodominant epitope. This result could not be achieved with conventional transcriptional control elements even after four consecutive immunizations. Moreover, the antigen-specific CD8 T cell response after three or more immunization rounds with the viruses according to the present invention was stronger than with a transcriptional control element conventionally used.

Unexpectedly, the stronger early expression of an antigen under control of a transcriptional control element comprising at least two elements driving early expression the control resulted in an even stronger presentation of antigen-derived peptide by MHC class I molecules on the surface of cells infected with a replication deficient recombinant virus.

Further to these surprising results associated with the use of replication deficient recombinant viruses according to the present invention, possible unwanted side effects, such as the induction of disease in the host are reduced to a minimum, thus rendering the use of replication deficient recombinant viruses as described herein highly advantageous vis-à-vis the use of replication competent recombinant viruses.

As used herein, the terms "antigen" or "antigenic epitope" are used to refer to a sequence which is specifically recognized or specifically bound by a component of the immune system. Generally, a protein antigen is highly variable in size and is recognized in the context of an MHC/HLA molecule to which a fragment of said protein antigen is bound on an antigen presenting cell. Thus, usually, the term "antigen" refers to a (longer) sequence, in particular a (longer) amino acid sequence or protein sequence, whereas the phrase "antigenic epitope" encompasses a (shorter) sequence, in particular an amino acid stretch or a peptide, respectively, that still elicits an immune response.

Preferably, said antigen and/or antigenic epitope is a cancer antigen or an antigen and/or antigenic epitope of an infectious agent, preferably selected from viruses, fungi, pathogenic unicellular eukaryotic and prokaryotic organisms, and parasitic organisms.

Particularly preferred examples of virus antigens suitable for use in the present invention comprise antigens from retroviruses (including HIV-1 and HTLV), herpesviruses (including cytomegalovirus), flaviviruses (including dengue virus), orthomyxoviruses, paramyxoviruses (including measles virus, mumps virus, respiratory syncytial virus), togaviruses (including rubella virus), hepatitis viruses, hepadnaviruses, influenza virus, picornaviruses (including such as poliovirus), coronaviruses, bunyaviruses, arenaviruses, filoviruses or from other viruses causing hemorrhagic fever.

Examples of preferred cancer antigens include prostate-specific antigen (PSA), prostatic acid phosphatase (PAP) antigen and Her-2/neu antigens.

Preferred bacterial antigens include anthrax antigens.

As used herein, the term "recombinant virus" refers to any virus that comprises an additional heterologous nucleic acid that is not naturally part of the viral genome as, e.g., a promoter according to the present invention. Said promoter may regulate expression of a viral own antigen or antigenic epitope and/or may regulate expression of a heterologous or recombinant gene. A heterologous or recombinant gene can be, e.g., a gene encoding a viral, bacterial, fungal or cancer antigen, a therapeutic gene, a gene coding for a peptide comprising at least one epitope to induce an immune response. Further examples for heterologous genes comprise an antisense expression cassette or a ribozyme gene.

As used herein, the term "replication deficient virus" denotes viruses which only have reduced capacity or have even lost their capacity to reproductively replicate in host cells. Preferably, the replication deficient viruses according to the present invention comprise viruses that do not replicate at all in the cells of the host, in particular in human cells, and which are, thus, replication incompetent. However, also those viruses are within the scope of the present invention that show a minor residual replication activity that is controlled by the immune system of the host.

Furthermore, the viruses used according to the present invention are preferably capable of infecting the host cell, but are substantially not capable or not capable at all of producing infectious progeny virus in the infected cells.

Viruses that are "capable of infecting cells" are viruses harboring on the viral surface structures capable of interacting with the host cells to such an extent that the virus or at least the viral genome is taken up into the host cell.

In the context of the present invention the term "virus not capable of producing infectious progeny virus in said cells" refers to viruses the genome of which is at least partially transcribed and translated into viral proteins or even replicated, however, not packaged into infectious viral particles. Thus, the viruses used according to the present invention are viruses leading to abortive infections in the host. Abortive infections may occur for two reasons: According to the first alternative a cell may be susceptible to infection but it may be non-permissive for multiplication of the virus, e.g. due to the fact that not all viral genes are expressed in a form necessary for multiplication of the virus in said cell. An example for this type of virus according to the present invention in human cells is Modified Vaccinia virus Ankara (MVA), which is explained in more detail below. According to the second alternative an abortive infection may also result from infection of cells with defective viruses, which lack a full complement of viral genes. An example for such a virus according to the present invention for human cells is DISC-HSV1 (disabled single-cycle Herpes simplex virus), i.e. a Herpes simplex virus, which is restricted to a single cycle of infection (Dilloo et al., A novel herpes vector for the high-efficiency transduction of normal and malignant human hematopoietic cells, Blood 89: 119-127, 1997). This virus lacks the gene for the essential glycoprotein H (gH), but can be grown to high titers in a complementing cell line expressing gH. In non-complementing cell lines that are permissive for herpes virus growth, it is restricted to a single cycle of replication, leading to the release of noninfectious virus.

The viruses according to the present invention are preferably capable of being replicated in at least one type of cells of at least one animal species. Thus, it is possible to amplify the virus prior to administration to the host that is to be vaccinated and/or treated. By way of example reference is made to MVA that can be amplified in CEF cells but which is not capable of producing infectious progeny virus in human cells.

Preferred embodiments of replication deficient viruses suitable for use according to the present invention include viruses of adenoviral, herpesviral and poxviral origin. Examples for a replication deficient adenovirus suitable for use in the present invention include an E1-deficient replication defective human adenovirus as described in Sharpe et al., Single oral immunization with replication deficient recombinant adenovirus elicits long-lived transgene-specific cellular and humoral immune response, Virology 293, 210-216, 2002. An example for a replication deficient Herpesvirus suitable for use in the context of the present invention includes DISC-HSV1 which has also already been mentioned above.

In a preferred embodiment, the replication deficient recombinant virus is a poxvirus, as, for example, an avipoxvirus or orthopoxvirus, such as vaccinia viruses.

Examples for avipoxviruses suitable for use in the present invention include any avipoxvirus such as Fowlpoxvirus, Canarypoxvirus, Uncopoxvirus, Mynahpoxvirus, Pigeonpoxvirus, Psittacinepoxvirus, Quailpoxvirus, Peacockpoxvirus, Penguinpoxvirus, Sparrowpoxvirus, Starlingpoxvirus and Turkeypoxvirus. Preferred avipoxviruses are Canarypoxvirus and Fowlpoxvirus. Avipoxviruses are naturally host-restricted and productively replicate only in avian species and cells (Taylor et al., Biological and immunogenic properties of a canarypox-rabies recombinant, ALVAC-RG (vCP65) in non-avian species, Vaccine 13 :539-549, 1995). If human cells are infected with an avipoxvirus, heterologous genes are expressed from the viral genome. However, the avipoxvirus does not replicate in the human cells and there is, thus, no risk that the human being is harmed by productive virus replication. Various recombinant avipoxviruses have been constructed that express e.g. lentiviral gene products (U.S. Pat. No. 5,766,598), cytokines and/or tumor-associated antigens (U.S. Pat. No. 5,833,975) or rabies G glycoprotein (Taylor et al., Biological and immunogenic properties of a canarypox-rabies recombinant, ALVAC-RG (vCP65) in non-avian species, Vaccine 13: 539-549, 1995). A recombinant canarypoxvirus expressing the four HIV genes gag, pol, env and nef has already been used in clinical trials (Peters, B. S., The basis for HIV immunotherapeutic vaccines, Vaccine 20: 688-705, 2001). Since avipoxviruses productively replicate only in avian cells, these cells have to be used for the amplification of the virus and for the generation of recombinant viruses.

An example for a canarypoxvirus is strain Rentschler. A plaque purified Canarypox strain termed ALVAC (U.S. Pat. No. 5,766,598) was deposited under the terms of the Budapest treaty with the American Type Culture Collection (ATCC), accession number VR-2547. Another Canarypox strain is the commercial canarypox vaccine strain designated LF2 CEP 524 24 10 75, available from Institute Merieux, Inc.

Examples of Fowlpoxviruses are strains FP-1, FP-5 and TROVAC (U.S. Pat. No. 5,766,598). FP-1 is a Duvette strain modified to be used as a vaccine in one day old chickens. The strain is a commercial fowlpoxvirus vaccine strain designated 0 DCEP 25/CEP67/2309 October 1980 and is available from Institute Merieux, Inc. FP-5 is a commercial fowlpoxvirus vaccine strain of chicken embryo origin available from American Scientific Laboratories (Division of Schering Corp.) Madison, Wis., United States Veterinary License No. 165, serial No. 30321.

In a particularly preferred embodiment of the invention, the replication deficient recombinant virus is an orthopoxvirus, such as a vaccinia virus. Examples for vaccinia viruses suitable for use in the present invention include the vaccinia virus strain DIs, which grows well in CEF cells but is unable to grow in most mammalian cells (Tagaya et al., A new mutant of dermovaccinia virus, Nature Vol. 192, No. 4800, 381-383, 1961; Ishii et al., Structural analysis of vaccinia virus DIs strain: Application as a new replication deficient viral vector, Virology 302, 433-444, 2002). Another preferred example of a suitable vaccinia virus is the highly attenuated vaccinia virus strain NYVAC, which was derived from a plaque-cloned isolate of the Copenhagen vaccine strain by deletion of 18 ORFs from the viral genome (Tartaglia et al., NYVAC: A highly attenuated strain of vaccinia virus, Virology 188, 217-232, 1992). NYVAC is characterized by a dramatically reduced ability to replicate in a variety of human tissue culture cells, but retains the ability to induce strong immune responses to extrinsic antigens.

While the invention is described in further detail with regard to recombinant vaccinia viruses, such as recombinant MVA, all the above-mentioned viruses are also equally suited for use in the present invention.

In a preferred embodiment of the invention, the replication deficient recombinant virus is a recombinant modified vaccinia virus Ankara (MVA).

MVA is related to Vaccinia virus, a member of the genus Orthopoxvirus in the family Poxviridae. MVA has been generated by more than 570 serial passages on chicken embryo fibroblasts of the dermal vaccinia strain Ankara (Chorioallantois vaccinia virus Ankara virus, CVA; for review see Mayr, A., et al., Passage History: Abstammung, Eigenschaften and Verwendung des attenuierten Vaccinia-Stammes MVA, Infection 3, 6-14, 1975), that was maintained in the Vaccination Institute, Ankara, Turkey for many years and used as the basis for vaccination of humans. However, due to the often severe post-vaccinal complications associated with vaccinia viruses, there were several attempts to generate a more attenuated, safer smallpox vaccine. During the period of 1960 to 1974, Prof. Anton Mayr succeeded in attenuating CVA by over 570 continuous passages in CEF cells (Mayr et al., Passage History: Abstammung, Eigenschaften and Verwendung des attenuierten Vaccinia-Stammes MVA. Infection 3: 6-14, 1975). It was shown in a variety of animal models that the resulting MVA was avirulent (Mayr, A. & Danner, K. Vaccination against pox diseases under immunosuppressive conditions, Dev. Biol. Stand. 41: 225-34, 1978). Additionally, this MVA strain has been tested in clinical trials as vaccine to immunize against the human smallpox disease (Mayr et al., Zbl. Bakt. Hyg. I, Abt. Org. B 167, 375-390 [1987], Stickl et al., MVA vaccination against smallpox: clinical tests with an attenuated live vaccinia virus strain (MVA) (author's transl), Dtsch. med. Wschr. 99, 2386-2392, 1974):

As part of the early development of MVA as a pre-smallpox vaccine, there were clinical trials using MVA-517 (corresponding to the 517th passage) in combination with Lister Elstree (Stickl, Smallpox vaccination and its consequences: first experiences with the highly attenuated smallpox vaccine "MVA". Prev. Med. 3(1): 97-101, 1974; Stickl and Hochstein-Mintzel, Intracutaneous smallpox vaccination with a weak pathogenic vaccinia virus ("MVA virus"). Munch Med. Wochenschr. 113: 1149-1153, 1971) in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with conventional vaccinia virus (Mayr et al., 1978, The smallpox vaccination strain MVA: marker, genetic structure, experience gained with the parenteral vaccination and behaviour in organisms with a debilitated defence mechanism (author's transl). Zentralbl. Bacteriol. (B) 167: 375-390). MVA-572 was deposited at the European Collection of Animal Cell Cultures as ECACC V94012707. MVA had diminished virulence while it maintained good immunogenicity.

Since many passages were used to attenuate MVA, there are a number of different strains or isolates, depending on the passage number in CEF cells. All MVA strains originate from Dr. Mayr and most are derived from MVA-572 that was used in Germany during the smallpox eradication program, or MVA-575 that was extensively used as a veterinary vaccine. MVA-575 was deposited on Dec. 7, 2000, at the European Collection of Animal Cell Cultures (ECACC) with the deposition number V00120707. The MVA-BN® product used as an example to generate recombinant MVA according to the present invention is derived from MVA-584 (corresponding to the 584th passage of MVA in CEF cells). A sample of MVA-BN® was deposited on Aug. 30, 2000, at the European Collection of Cell Cultures (ECACC) under number V00083008.

As a consequence of the long-term passages of the parental chorioallantois vaccinia virus Ankara (CVA) the genome of the resulting MVA virus showed deletions of about 27 kilobases of its genomic sequence and, therefore, was described as highly host cell restricted to avian cells (Meyer, H. et al., Mapping of deletions in the genome of the highly attenuated vaccinia virus MVA and their influence on virulence, J. Gen. Virol. 72, 1031-1038, 1991). The attenuated strains lack approximately 13% (about 26.5 kb from six major and multiple minor deletion sites) of the coding region of the genome compared to ancestral CVA virus (Meisinger-Henschel et al., Genomic sequence of chorioallantois vaccinia virus Ankara, the ancestor of modified vaccinia virus Ankara, J. Gen. Virol. 88, 3249-3259, 2007.) The deletions affect a number of virulence and host range genes, as well as a large fragment of the gene coding for A-type inclusion protein (ATI) and a gene coding for a structural protein directing mature virus particles into A-type inclusion bodies.

The invention, thus, encompasses replication deficient recombinant MVA viruses generated with any and all MVA viruses. Accordingly, MVA strain deposit VR-1508, deposited at the American Type Culture collection (ATCC), Manassas, Va. 20108, USA, as well as the MVA virus strains mentioned above, namely strains MVA 572 and 575 deposited at the European Collection of Animal Cell Cultures (ECACC), Salisbury (UK) with the deposition number ECACC V94012707 and ECACC V00120707, respectively, are preferred according to the present invention. Particularly preferred MVA viruses are MVA strains MVA-BN® as, e.g., deposited at ECACC under number V00083008 and derivatives or variants having the same properties as MVA-BN.

MVA-BN® can attach to and enter human cells where virally-encoded genes are expressed very efficiently. However, assembly and release of progeny virus does not occur. Preparations of MVA-BN® and derivatives have been administered to many types of animals, and to more than 2000 human subjects, including immunodeficient individuals. All vaccinations have proven to be generally safe and well tolerated.

The perception from many different publications is that all MVA strains are the same and represent a highly attenuated, safe, live viral vector. However, preclinical tests have revealed that MVA-BN® demonstrates superior attenuation and efficacy compared to other MVA strains (WO 02/42480): The MVA variant strains MVA-BN® as, e.g., deposited at ECACC under number V00083008 have the capability of reproductive replication in vitro in chicken embryo fibroblasts (CEF), but no capability of reproductive replication in human cells in which MVA 575 or MVA 572 can reproductively replicate. For example, MVA-BN® has no capability of reproductive replication in the human keratinocyte cell line HaCaT, the human embryo kidney cell line 293, the human bone osteosarcoma cell line 143B, and the human cervix adenocarcinoma cell line HeLa. Further, MVA-BN® strains fail to replicate in a mouse model that is incapable of producing mature B and T cells, and as such is severely immune-compromised and highly susceptible to a replicating virus. An additional or alternative property of MVA-BN® strains is the ability to induce at least substantially the same level of immunity in vaccinia virus prime/vaccinia virus boost regimes when compared to DNA-prime/vaccinia virus boost regimes.

Thus, in a preferred embodiment, the MVA according to the invention has the capability of reproductive replication in vitro in chicken embryo fibroblasts (CEF), but no capability of reproductive replication in human cells in which MVA 575 or MVA 572 can reproductively replicate. Most preferably, the MVA has no capability of reproductive replication in the human keratinocyte cell line HaCaT, the human embryo kidney cell line 293, the human bone osteosarcoma cell line 143B, and the human cervix adenocarcinoma cell line HeLa. Thus, in a most preferred embodiment, the MVA strain used in the present invention is MVA-BN® as deposited at ECACC under number V00083008 and derivatives thereof and variants revealing the same properties as described for MVA-BN, respectively.

The features of MVA-BN, the description of biological assays allowing evaluating whether an MVA strain is MVA-BN or a derivative thereof and methods allowing to obtain MVA-BN or an MVA having the properties of MVA-BN are disclosed in WO 02/42480. Said reference also discloses how MVA and other vaccinia viruses can be propagated. Briefly, eukaryotic cells are infected with the virus. The eukaryotic cells are cells that are susceptible to infection with the respective poxvirus and allow replication and production of infectious virus. For MVA an example for this type of cells are chicken embryo fibroblasts (CEF) and BHK cells (Drexler et al., Highly attenuated modified vaccinia Ankara replicates in baby hamster kidney cells, a potential host for virus propagation, but not in various human transformed and primary cells, J. Gen. Virol. 79, 347-352, 1998). CEF cells can be cultivated under conditions known to the person skilled in the art. Preferably the CEF cells are cultivated in serum-free medium in stationary flasks or roller bottles. The incubation preferably takes place 48 to 96 hours at 37° C. For the infection MVA is preferably used at a multiplicity of infection (MOI) of 0.05 to 1 TCID50 and the incubation preferably takes place 48 to 72 hours at 37° C.

The term "not capable of reproductive replication" is used in the present application as defined in WO 02/42480 and U.S. Pat. No. 6,761,893, which are hereby incorporated by reference. Thus, said term applies to a virus that has a virus amplification ratio at 4 days after infection of less than 1 using the assays described in U.S. Pat. No. 6,761,893, which assays are hereby incorporated by reference. The "amplification ratio" of a virus is the ratio of virus produced from an infected cell (Output) to the amount originally used to infect the cells in the first place (Input). A ratio of "1" between Output and Input defines an amplification status wherein the amount of virus produced from the infected cells is the same as the amount initially used to infect the cells.

MVA-BN® or its derivatives are, according to one embodiment, characterized by inducing at least substantially the same level of immunity in vaccinia virus prime/vaccinia virus boost regimes when compared to DNA-prime/vaccinia virus boost regimes. A vaccinia virus is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in WO 02/42480, preferably in both assays, is at least substantially the same in vaccinia virus prime/vaccinia virus boost regimes when compared to DNA-prime/vaccinia virus boost regimes. More preferably, the CTL response after vaccinia virus prime/vaccinia virus boost administration is higher in at least one of the assays, when compared to DNA-prime/vaccinia virus boost regimes. Most preferably, the CTL response is higher in both assays.

WO02/42480 discloses how vaccinia viruses are obtained having the properties of MVA-BN®. The highly attenuated MVA-BN virus can be derived, e.g., by the further passage of a modified vaccinia virus Ankara (MVA), such as MVA-572 or MVA-575 and, optionally, by additional plaque purification step(s).

In summary, MVA-BN® has been shown to have the highest attenuation profile compared to other MVA strains and is safe even in severely immunocompromised animals.

Although MVA is strongly replication-restricted in mammalian cells, its genes are efficiently transcribed, with the block in viral replication being at the level of virus assembly and egress. (Sutter and Moss, Nonreplicating vaccinia vector efficiently expresses recombinant genes. Proc. Natl. Acad. Sci. U.S.A 89: 10847-10851, 1992; Carroll and Moss, Host range and cytopathogenicity of the highly attenuated MVA strain of vaccinia virus: propagation and generation of recombinant viruses in a nonhuman mammalian cell line. Virology 238: 198-211, 1997.) Despite its high attenuation and reduced virulence, in preclinical studies MVA-BN® has been shown to elicit both humoral and cellular immune responses to VACV and to the products of heterologous genes cloned into the MVA genome (Harrer et al., Therapeutic Vaccination of HIV-1-infected patients on HAART with recombinant HIV-1 nef-expressing MVA: safety, immunogenicity and influence on viral load during treatment interruption. Antiviral Therapy 10: 285-300, 2005; Cosma et al., Therapeutic vaccination with MVA-HIV-1 nef elicits Nefspecific T-helper cell responses in chronically HIV-1 infected individuals. Vaccine 22(1): 21-29, 2003; Di Nicola et al., Clinical protocol. Immunization of patients with malignant melanoma with autologous CD34(+) cell-derived dendritic cells transduced ex vivo with a recombinant replication-deficient vaccinia vector encoding the human tyrosinase gene: a phase I trial. Hum Gene Ther. 14(14): 1347-1 360, 2003; Di Nicola et al., Boosting T cell-mediated immunity to tyrosinase by vaccinia virus-transduced, CD34(+)-derived dendritic cell vaccination: a phase I trial in metastatic melanoma. Clin Cancer Res. 10(16): 5381-5390, 2004.)

MVA-BN® and recombinant MVA-BN®-based vaccines can be generated, passaged, produced and manufactured in CEF cells cultured in serum-free medium. Many recombinant MVA-BN® variants have been characterized for preclinical and clinical development. No differences in terms of the attenuation (lack of replication in human cell lines) or safety (preclinical toxicity or clinical studies) have been observed between MVA-BN®, the viral vector backbone, and the various recombinant MVA-based vaccines.

According to the present invention, the replication deficient recombinant viruses comprise an antigen and/or antigenic epitope wherein expression of said antigen and/or antigenic epitope, respectively, is regulated by a transcriptional control element.

As used herein, transcriptional control elements or sequences are DNA regulatory sequences, such as promoter sequences to bind RNA polymerase, enhancers, translation initiation sequences for ribosome binding and/or terminators, and the like, that provide for the expression of an antigen of interest in a host cell.

In a preferred embodiment, the replication deficient recombinant virus comprises as transcriptional control element which comprises at least two elements driving early expression of the antigen and/or antigenic epitope of interest. Said at least two elements may be promoter elements, preferably early promoter elements, more preferably at least two, most preferably at least five copies of an early promoter element.

As used herein, the terms "early promoter" or "early promoter element" refer to promoters that are active in virus infected cells before viral DNA replication has occurred.

Methods are known to the person skilled in the art how it can be determined whether a promoter is an early promoter. In particular, the promoter of interest can be inserted upstream of a reporter gene and said construct can be introduced into a viral vector, e.g. a vaccinia virus vector which is then used to infect cells. In order to assess the activity as early promoter the cells are incubated with a substance that inhibits viral DNA replication such as AraC. DNA replication is a prerequisite for the late promoter activity. Thus, any promoter activity that is measured in this assay system is due to elements active as early promoter. Consequently, the term "late promoter" refers to any promoter that is active after DNA replication has taken place. The late activity can also be measured by methods known to the person skilled in the art. For the sake of simplicity the term "late promoter" as used in the present application refers to a promoter that is only active if no substance is added that blocks DNA replication.

In a preferred embodiment, the replication deficient recombinant virus comprises an early/late promoter, preferably a poxvirus early/late promoter. An early/late promoter drives expression of a linked nucleic acid sequence at both early and late times of the viral lifecycle.

Preferably, the early/late promoter comprises at least one late promoter element linked to at least two, three, four, five, six, seven, eight, nine, ten, eleven, twelve, thirteen, fourteen, fifteen or more copies of an early promoter element.

Even more preferably, said early/late promoter comprises a late promoter element and at least two, preferably at least five copies of an early promoter element, preferably copies of a nucleotide sequence element according to nucleotide (nt) 48-81 of SEQ ID NO:1.

In another preferred embodiment, the at least two elements of the transcriptional control element, in particular the at least two, preferably at least five copies of the early promoter element are sequence optimized.

In a further preferred embodiment, said early/late promoter is an early/late hybrid promoter comprising a late element derived from a promoter different to the one from which the early element is derived.

The inventors of the present invention have surprisingly found that a transcriptional control element driving expression of an antigen as early and as strong as possible provides the antigen with a temporal and quantitative advantage over the majority of autochthonous vector antigens and thus is beneficial for induction of a strong antigen-specific T cell response, in particular a CD8 T cell response.

A strong early promoter was designed for MVA which was used as an example and as a preferred embodiment of a replication deficient recombinant virus according to the present invention. To design a strong early promoter, a combination of multiple early promoter elements in a tandem fashion was used to enhance expression specifically in the early phase of the viral replication cycle. This promoter element was coupled to a short late promoter element derived from the cowpox ATI promoter which is supposed to direct gene expression in the late phase and lead to a further increase in the amount of expressed antigen.

The kinetics of expression was shifted towards earlier time points using a promoter belonging to the recently defined class of immediate early promoters. Immediate early genes are defined as being expressed in the period starting 0.5 to 1 hour after infection. (Assarsson et al., Kinetic analysis of a complete poxvirus transcriptome reveals an immediate-early class of genes. Proc. Natl. Acad. Sci. U.S.A 105:2140-2145, 2008; Davison, A. J. and B. Moss, Structure of vaccinia virus early promoters. J. Mol. Biol. 210:749-769, 1989.). The transcriptional control element according to the present invention is, most preferably, an immediate early transcriptional control element designed by combining at least two, preferably five or even a multimer of early transcriptional control elements, which are preferably sequence optimized, in a tandem fashion. Said early transcriptional control element is preferably designed by an early promoter element, most preferably by a poxvirus early promoter element. Preferably, said early promoter element is a p7.5 early promoter element, most preferably a sequence optimized p7.5 early promoter element.

Preferably, the poxvirus early/late promoter comprises at least one late promoter element linked to at least two, three, four, five, six, seven, eight, nine, ten, eleven, twelve, thirteen, fourteen, fifteen or more copies of an early promoter element.

Even more preferably, said poxvirus early/late promoter comprises a late promoter element and at least two, preferably at least five copies of an early promoter element, preferably copies of a nucleotide sequence element according to nt 48-81 of SEQ ID NO:1.

Particularly preferred is a poxvirus early/late promoter comprising at least two, preferably at least five copies of a p7.5 early promoter element, more preferably copies of a sequence optimized p7.5 early promoter element.

Preferably, the poxvirus early/late promoter is a poxvirus early/late hybrid promoter comprising a late element derived from a promoter different to the one from which the early element is derived.

According to a further preferred embodiment, the late element of the poxvirus early/late hybrid promoter is or comprises the cowpox ATI late promoter.

Preferably, the poxvirus early/late hybrid promoter comprises at least one late promoter element, preferably an ATI promoter element, linked to at least two, three, four, five, six, seven, eight, nine, ten, eleven, twelve, thirteen, fourteen, fifteen or more copies of an early promoter element, preferably a p7.5 early promoter element and most preferably a sequence optimized p7.5 early promoter element.

Particularly preferred is a replication deficient recombinant virus as defined above wherein said poxvirus early/late hybrid promoter comprises the nucleotide sequence of SEQ ID NO:1.

The sequence of the promoter of the cowpox virus A-type inclusion protein gene (ATI promoter) is known to the person skilled in the art. In this context reference is made to the Genebank entry accession number D00319. A preferred ATI promoter sequence is as follows: 5'GTTTT GAATA AAATT TTTTT ATAAT AAAT 3' (SEQ ID NO:6).

According to the present invention it is possible to use the ATI promoter as specified above or to use a derivative of the ATI promoter, which may be a subsequence of the sequence shown above. The term "subsequence" refers to shorter fragments of the sequence shown above that are still active as a promoter, in particular as vaccinia virus late promoter. A typical fragment of the sequence of the ATI promoter has a length of at least 10 nucleotides, more preferably of at least 15 nucleotides, even more preferably of at least 20 nucleotides, most preferably of at least 25 nucleotides of the sequence of the ATI promoter. The subsequence preferably may comprise nucleotides 25 to 29 of the ATI sequence i.e. the sequence 5'-TAAAT-3' located at the 3' end of the ATI promoter sequence. The subsequence may also comprise nucleotides 22 to 29 of the ATI promoter sequence, i.e. the sequence 5-TAATAAAT-3' located at the 3' end of the ATI promoter sequence.

of an ATI late promoter (hereinafter denoted as "pHyb promoter") did not only occur significantly earlier, but was also significantly higher than expression driven by the well-defined synthetic promoter pS and the p7.5 promoter at times of between 30 and 120 min after infection. Significant amounts of eGFP were detected already at 30 min after infection. This was two to three times faster than with the established early/late pS or p7.5 promoters. Combination of at least three immunization rounds with such an immediate-early promoter for expression of an antigen resulted in an increased antigen-specific CD8 T cell response compared to the conventional poxviral p7.5 and pS promoter. The advantage in strong early antigen expression persisted until at least 6 h after infection. Thus, early gene expression was exceedingly high from this promoter.

In preferred embodiments, the recombinant MVA expresses high levels of the encoded antigen and/or antigenic epitope during the immediate early phase of viral replication. In some embodiments, recombinant MVA expresses in HeLa cells a level of the encoded antigen in the presence of 40 µg/ml AraC that is within 10%, 20%, or 50%, or that is at least 50%, 55%, 60%, 65%, 70%, 75%, 80%, 85%, 90%, 95%, or 100% of the level of the encoded antigen in the absence of AraC. In preferred embodiments, recombinant MVA expresses in HeLa cells a level of the encoded antigen in the presence of 40 µg/ml AraC that is higher than the level of the encoded antigen in the absence of AraC. In various embodiments, the recombinant MVA expresses twofold, three-fold, or four-fold higher levels of the encoded antigen than an MVA vector with the pS promoter driving expression in HeLa and/or CEF cells in the presence of 40 µg/ml AraC.

In a preferred embodiment, the early/late hybrid promoter comprises the following sequence:

```
                                                               (SEQ ID NO: 1)
5'acgcgtgtttaaacgttttgaaaatttttttataataaatatccggtaaaaattgaaaaactattctaatttattg cacggtccggtaaaaattgaaaaactattctaatttattgcacggtccggtaaaaattgaaaaactattctaat ttattgcacggtccggtaaaaattgaaaaactattctaatttattgcacggtccggtaaaaattgaaaaactatt ctaatttattgcacggtccgga 3'.
```

The early element of the p7.5 promoter was optimized by single nucleotide substitution, which is described in further detail below. Optimization resulted in a promoter with higher expression in the presence of AraC than in the absence of AraC in HeLa cells. Furthermore, expression of enhanced GFP (eGFP) driven by a promoter comprising five copies of the optimized p7.5 early promoter element linked to one copy The sequence of the ATI late promoter is in italics, while the 5 copies of the optimized p7.5 early promoter are underlined. Optimization of the p7.5 early promoter was carried out according to Davison & Moss, Structure of Vaccinia Virus Early Promoters, J. Mol. Biol. 210, 749-769, 1989.

The elements of the optimized pHyb promoter (SEQ ID NO:1) are as follows:

```
5'acgcgtgtttaaac                    MluI/PmeI restriction site
(nt 1-14 of SEQ ID NO: 1)

gttttgaaaatttttttataataaata         ATI late promoter
(nt 15-41 of SEQ ID NO: 1)

tccggt                              Linker
(nt 42-47 of SEQ ID NO: 1)

aaaaattgaaaaactattctaatttattgcacgg  P7.5 early optimized
(nt 48-81 of SEQ ID NO: 1)

tccggt                              Linker
(nt 82-87 of SEQ ID NO: 1)

aaaaattgaaaaactattctaatttattgcacgg  P7.5 early optimized
(nt 88-121 of SEQ ID NO: 1)
```

-continued

```
tccggt                                Linker
(nt 122-127 of SEQ ID NO: 1)

aaaaattgaaaaactattctaatttattgcacgg    P7.5 early optimized
(nt 128-161 of SEQ ID NO: 1)

tccggt                                Linker
(nt 162-167 of SEQ ID NO: 1)

aaaaattgaaaaactattctaatttattgcacgg    P7.5 early optimized
(nt 168-201 of SEQ ID NO: 1)

tccggt                                Linker
(nt 202-207 of SEQ ID NO: 1)

aaaaattgaaaaactattctaatttattgcacgg    P7.5 early optimized
(nt 208-241 of SEQ ID NO: 1)

tccgga 3'                             BspEI restriction site
(nt 242-247 of SEQ ID NO: 1).
```

In further embodiments, the early/late hybrid promoter comprises a sequence that is at least 80%, 85%, 90%, 95%, 98% or 99% homologous or identical to the nucleotide sequence of SEQ ID NO:1 or to nt 15-41 or nt 48-81, nt 48-87, or nt 48-247 of SEQ ID NO:1. Based on knowledge of the consensus sequences of early and late promoters, as well as knowledge regarding the effects of various nucleotide substitutions on early and late promoter activity (Davison and Moss, Structure of Vaccinia Virus Early Promoters, J. Mol. Biol. 210, 749-769, 1989.), many changes to the promoter sequence of SEQ ID NO:1 can be envisioned that would not negatively affect the activity of the promoter. Nucleotide sequences that differ from SEQ ID NO:1 in one or more positions, but have substantially the same (i.e., within a range of about +/−20%) early and late promoter activity as that of the promoter SEQ ID NO:1 are encompassed by the present invention.

In a further preferred embodiment, the invention relates to a promoter comprising at least 2 nucleotide sequence elements having at least 80%, 85%, 90%, 95%, 98%, 99%, or even 100% homology or identity to nt 48-81 of SEQ ID NO:1. In a particularly preferred embodiment, the promoter comprises at least 2, preferably at least 5 nucleotide sequence elements according to nt 48-81 of SEQ ID NO:1. Preferably, the promoter comprises at least one late promoter element, preferably a cowpox ATI late promoter element.

The percent sequence identity may be determined by visual inspection and mathematical calculation. Alternatively, the percent identity of two nucleic acid sequences can be determined by comparing sequence information using the GAP computer program, version 6.0 described by Devereux et al. (Nucl. Acids Res. 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps. Other programs used by one skilled in the art of sequence comparison may also be used.

The present invention also relates to the replication deficient recombinant virus as defined above for use as medicament or vaccine and the use of the replication deficient recombinant virus as defined above for the preparation of a medicament or vaccine.

The replication deficient recombinant virus according to the present invention is administered in a concentration range of $10^2$ to $10^9$, or $10^4$ to $10^9$ TCID (tissue culture infectious dose) 50/ml, preferably in a concentration range of e.g. $10^5$ to $5 \times 10^8$ TCID50/ml, more preferably in a concentration range of e.g. $10^6$ to $10^8$ TCID50/ml, most preferably in a concentration range of e.g. $10^7$ to $10^8$ TCID50/ml, or at least $2-5 \times 10^7$ to $10^8$ or $2-5 \times 10^8$ to $10^9$, especially $10^8$ TCID50/ml. The actual concentration depends on the type of virus used and the animal species to be vaccinated. A preferred vaccination dose for humans comprises $10^6$ to $10^9$ TCID50, more preferably a dose of $10^7$ or $10^8$ TCID50, most preferably a dose of $10^8$ TCID50 or more, in particular 2 or $2.5-5 \times 10^8$ or $10^9$. For MVA-BN a typical vaccination dose for humans comprises $5 \times 10^7$ TCID50 to $5 \times 10^8$ TCID50, such as about 1, 2, or $2.5 \times 10^8$ TCID50, administered subcutaneously.

It is possible to induce an immune response with a single administration of the replication deficient recombinant virus as defined above, for example with MVA, in particular with strain MVA-BN and its derivatives. Usually one may use the replication deficient recombinant virus according to the present invention, for example MVA, in particular MVA-BN and its derivatives in homologous prime boost regimes, i.e. it is possible to use a recombinant virus for a first vaccination and to boost the immune response generated in the first vaccination by administration of the same or a related recombinant virus than the one used in the first vaccination. Homologous prime/boost administration is also a preferred embodiment of the present invention.

The replication deficient recombinant virus according to the present invention, for example MVA, in particular MVA-BN and its derivatives may also be used in heterologous prime-boost regimes in which one or more of the vaccinations is done with a virus as defined above and in which one or more of the vaccinations is done with another type of vaccine, e.g. another virus vaccine, a protein or a nucleic acid vaccine.

The mode of administration may be intravenously, intramuscularly, intradermally, intranasally, or subcutaneously. Preferred is intravenous, intramuscular or, in particular, subcutaneous administration. However, any other mode of administration may be used such as scarification.

The invention also relates to a pharmaceutical composition or vaccine comprising the replication deficient recombinant virus as defined above and, optionally, a pharmaceutically acceptable carrier, diluent, adjuvant and/or additive.

Numerous ways to prepare viral formulations are known to the skilled artisan as well as modes of storage. In this context and in particular for the preparation of poxviral formulations reference is made to WO 03053463.

Non-limiting examples of auxiliary substances are water, saline, glycerol, ethanol, wetting or emulsifying agents, pH buffering substances, preservatives, stabilizers, or the like. Suitable carriers are typically selected from the group comprising large, slowly metabolized molecules such as, for example, proteins, polysaccharides, polylactic acids, polyglycolitic acids, polymeric amino acids, amino acid copolymers, lipid aggregates, or the like.

For the preparation of vaccines, the recombinant MVA virus according to the invention is converted into a physiologically acceptable form. Suitable preparations depend on the type of virus and are known to the skilled person. For poxvirus vaccines this can be done based on the experience in the preparation of smallpox vaccines (as described by Stickl, H. et al. Dtsch. med. Wschr. 99, 2386-2392 [1974]). For example, the purified virus is stored at −80° C. with a titer of 5×10⁸ TCID50/ml formulated in 10 mM Tris, 140 mM NaCl pH 7.4.

In one embodiment, the replication deficient recombinant virus according to the invention is used for the preparation of vaccine shots. For example, about 10² to about 10⁸ particles of the virus are lyophilized in 100 ml of phosphate-buffered saline (PBS) in the presence of 2% peptone and 1% human albumin in an ampoule, preferably a glass ampoule. In another non-limiting example, the vaccine shots are produced by stepwise freeze-drying of the virus in a formulation. In certain embodiments, this formulation can contain additional additives such as mannitol, dextran, sugar, glycine, lactose or polyvinylpyrrolidone or other aids, such as antioxidants or inert gas, stabilizers or recombinant proteins (for example, human serum albumin) suitable for in vivo administration. The glass ampoule is then sealed and can be stored between 4° C. and room temperature for several months. However, as long as no immediate need exists, the ampoule is stored preferably at temperatures below −20° C.

For vaccination or therapy, the lyophilisate may be dissolved in 0.1 to 0.5 ml of an aqueous solution, preferably physiological saline or Tris buffer, and administered either systemically or locally, i.e. parenterally, subcutaneously, intramuscularly, by scarification or any other path of administration know to the skilled practitioner. The mode of administration, the dose and the number of administrations can be optimized by those skilled in the art in a known manner. However, most commonly, a patient is vaccinated with a second shot about one month to six weeks after the first vaccination shot. A third, a fourth and subsequent shots can be given usually 4-12 weeks, preferably 4-6 weeks after the previous administration.

In one embodiment, a subject mammal, which included rats, rabbits, mice, and humans are immunized comprising administering a dosage of the recombinant replication deficient virus, in particular MVA, to the subject, preferably a human. In one embodiment, the first dosage as well as the second and additional dosages (i.e., third, fourth, fifth, etc.) especially of a recombinant MVA comprise preferably 10⁸ TCID50 of the recombinant virus.

In another aspect the present invention relates to the replication deficient recombinant virus or the pharmaceutical composition or vaccine as defined above for inducing a T cell response in a host to said at least one antigen and/or antigenic epitope.

Further, the present invention relates to the use of the replication deficient recombinant virus or the pharmaceutical composition or vaccine as defined above for the preparation of a medicament for inducing a T cell response in a host to said at least one antigen and/or antigenic epitope.

In a preferred embodiment said T cell response is a CD8 T cell response.

Immunizations with the replication deficient recombinant virus of the invention, in particular with the recombinant MVA, can affect robust CD8 T cell responses. In preferred embodiments, after the first prime and at least two boost administrations, wherein administration takes place at intervals of at least one week, the recombinant MVA affects a CD8 T cell response in the host against the encoded antigen that is greater than the CD8 T cell response against an immunodominant CD8 T cell epitope encoded by the MVA vector backbone. Preferably, the CD8 T cell response against the antigen driven by an optimized hybrid early/late promoter according to the present invention is increased compared to the response against the same antigen driven by a synthetic strong pS promoter or similar early/late promoters. Preferably, after the third, fourth, fifth, etc. administration, an immunodominant T cell response is exerted in the host against the encoded antigen, i.e., a CD8 T cell epitope derived from the recombinant antigen is converted into the immunodominant epitope. Most preferably, after the third, fourth, fifth, etc. administration, the recombinant MVA induces a CD8 T cell response in the host against the encoded antigen that is at least 10%, 15%, 20%, 25%, 30%, or 35% of total CD8 T cells.

In a preferred embodiment, the CD8 T cell response against the recombinant antigen induced after the third, fourth, fifth, etc. administration of the recombinant MVA comprising an optimized hybrid early/late promoter according to the present invention is at least 20% higher than the CD8 T cell response affected after administration of a recombinant MVA comprising the pS promoter. In further preferred embodiments, the CD8 T cell response affected after the third, fourth, fifth etc. administration is 30%, 40%, 50%, 60%, 70%, 80%, 90% higher. In the most preferred embodiment, the affected CD8 T cell response is 100% higher.

As used herein, the term "affecting a T cell response" is to be understood that a T cell response is induced, raised and/or enhanced.

The replication deficient recombinant virus according to the invention can be used for the treatment of a wide range of mammals including humans and even immune-compromised humans.

In preferred embodiments, the treatment comprises at least three, four, five or even more administrations (corresponding to a first prime followed by at least two, three, four, five or even more boost administrations) of a replication deficient recombinant virus, preferably a recombinant MVA, to the host. Administration of the recombinant virus is accomplished as prime-boost administration, i.e. said at least three administrations comprise a first inoculation (prime inoculation/immunization) followed by a second and third inoculation (boosting inoculations/immunizations).

In the context of the present invention the term "host" encompasses any suitable animal species, in particular a vertebrate animal. Preferred are mammals including humans. Further specific examples for animals are pets such as dogs, cats, economically important animals such as calves, cattle, sheep, goats, horses, pigs and other animal such as mice, rats. For these animal species and for humans MVA and DISC-HSV are particularly preferred viruses. The invention may also be used for economically important birds such as turkeys, ducks, goose and hens if viruses are used that are capable to infect the bird's cells but not capable of producing infectious progeny virus in said cells.

The T cell response to said at least one antigen and/or antigenic epitope may be induced by heterologous prime-boost regimes in which one or more of the vaccinations is done with a virus as defined above and in which one or more of the vaccinations is done with another type of vaccine, e.g. another virus vaccine, a protein or a nucleic acid vaccine. However, preferably said T cell response is induced by homologous prime/boost regimes in which the same or a related replication deficient recombinant virus is used for both prime and boost vaccinations.

Accordingly, in another preferred embodiment said T cell response is induced by an immunization regimen comprising homologous prime/boost administrations.

In further embodiments said T cell response is induced by an immunization regimen comprising at least three or at least four administrations of the replication deficient recombinant virus or the pharmaceutical composition or vaccine as defined above.

The present invention also encompasses a kit comprising at least two vials for prime/boost immunization comprising said replication deficient recombinant virus for a first inoculation ("priming inoculation") in a first vial/container and for an at least second and/or third and/or further inoculation ("boosting inoculation") in a second and/or further vial/container.

The kit may comprise at least one, two, three, four, or more containers or vials of the recombinant virus, together with instructions for the administration of the virus to a subject. In a preferred embodiment, the subject is a human. The instructions may indicate that the recombinant virus is administered to the subject in multiple (i.e., 2, 3, 4, 5, 6, etc.) dosages at specific timepoints (e.g., at least 4 weeks, at least 6 weeks, at least 8 weeks after the previous administration). Preferably, the instructions indicate that the recombinant virus is to be administered in at least 3 or at least 4 dosages.

If the vaccine is a MVA-BN vector or derivative thereof comprising a DNA according to the present invention a particular embodiment of the present invention concerns a kit for vaccination comprising an MVA-BN virus vector according to the present invention for the first vaccination ("priming") in a first vial/container and for a at least second vaccination and third vaccination ("boosting") in a second/third vial/container.

EXAMPLES

The following examples will further illustrate the present invention. It will be well understood by a person skilled in the art that the provided examples in no way may be interpreted in a way that limits the applicability of the technology provided by the present invention to this examples.

Statistical analysis of data was done using a two-way repeated measures ANOVA test if not indicated otherwise.

Example 1

Generation of MVA-BN Recombinants

A hybrid late/early promoter designated pHyb containing a late element from the cowpox virus ATI promoter and five tandemly arranged early promoter elements was constructed (FIG. 1). The early promoter elements were based on the p7.5 promoter and further optimized using published data (Broyles, S. S. 2003. Vaccinia virus transcription. J. Gen. Virol. 84:2293-2303; Chakrabarti, S., J. R. Sisler, and B. Moss. 1997. Compact, synthetic, vaccinia virus early/late promoter for protein expression. Biotechniques 23:1094-1097; Davison, A. J. and B. Moss. 1989. Structure of vaccinia virus early promoters. J. Mol. Biol. 210:749-769). The pHyb promoter was compared with the widely-used synthetic pS promoter which directs high level gene expression and with the natural p7.5 promoter (Cochran, M. A., C. Puckett, and B. Moss. 1985. In vitro mutagenesis of the promoter region for a vaccinia virus gene: evidence for tandem early and late regulatory signals. J. Virol. 54:30-37) (FIG. 1). These promoter constructs were cloned upstream of the open reading frames for either chicken ovalbumine (OVA) or eGFP and introduced into the genomes of MVA viruses by homologous recombination.

The pHyb promoter was assembled using a late element from the promoter directing the expression of the A-type inclusion (ATI) protein in cowpox virus (Funahashi, S., T. Sato, and H. Shida. 1988. Cloning and characterization of the gene encoding the major protein of the A-type inclusion body of cowpox virus. J. Gen. Virol. 69 (Pt 1):35-47; Patel, D. D., C. A. Ray, R. P. Drucker, and D. J. Pickup. 1988. A poxvirus-derived vector that directs high levels of expression of cloned genes in mammalian cells. Proc. Natl. Acad. Sci. U.S. A 85:9431-9435). The five tandemly arranged early elements were derived from the p7.5 promoter and were modified at 4 nucleotide positions within the A-rich critical core region of 16 nucleotides as described (Davison, A. J. and B. Moss. 1989. Structure of vaccinia virus early promoters. J. Mol. Biol. 210:749-769). The natural p7.5 promoter used here consisted of a 104 base pair-long DNA fragment containing the late and the early promoter element. The sequence of the strong synthetic early/late pS promoter comprised 40 nucleotides exactly matching the sequence that was previously described (Chakrabarti, S., J. R. Sisler, and B. Moss. 1997. Compact, synthetic, vaccinia virus early/late promoter for protein expression. Biotechniques 23:1094-1097). Recombinant MVAs were generated using a cloned version of the MVA-BN genome in a bacterial artificial chromosome (BAC). Briefly, the pHyb and pS promoter constructs were cloned upstream of the open reading frames for either chicken ovalbumine (OVA) or enhanced green fluorescent protein (eGFP). These expression cassettes were flanked with homology arms of approximately 45 nucleotides by PCR and introduced into the intergenic region between genes MVA136 and MVA137 by homologous recombination to obtain recombinant MVA-BACs. Infectious viruses were reconstituted from BACs by transfecting BAC DNA into BHK-21 cells and superinfecting with shope fibroma virus as helper virus. After three passages on CEF cells, helper-free viruses (confirmed by PCR) MVA-pHyb-eGFP and MVA-pHyb-OVA expressing either eGFP or OVA under control of the pHyb promoter and MVA-pS-eGFP and MVA-pS-OVA expressing eGFP or OVA under control of the pS promoter were obtained.

Example 2

Cell Culture and Cell Cycle Arrest by AraC

Primary chicken embryo fibroblast (CEF) cells were prepared from 11-day old embryos and cultured in VP-SFM (serum-free medium; Invitrogen, Karlsruhe, Germany). HeLa and EL4 cells were cultured in DMEM/10% FCS (Invitrogen). Cells were infected with 10 TCID50 per cell of the MVA recombinants expressing eGFP under control of the indicated promoters. After the indicated time points, infected cells were harvested by trypsinization and analyzed by flow cytometry for eGFP expression levels using an LSR II flow cytometry analyzer (BD Biosciences, Heidelberg, germany). Where indicated, cytosine arabinoside (AraC) was added to the medium throughout infection at a final concentration of 40 μg/ml to arrest MVA replication in the early phase.

Example 3

Immunization of Mice

Female C57BL/6 mice aged 6 to 8 weeks were purchased from Harlan Winkelmann, Germany. Groups of 5 mice were immunized via the intraperitoneal route with an inoculum of 200 μl containing $10^8$ $TCID_{50}$ of the respective MVA recombinants at weeks 0, 4, 8 and either weeks 12 or 22 for T cell analysis and weeks 0, 2, and 4 for analysis of anti-OVA and anti-MVA antibodies. Blood was taken via the tail vein at the indicated time points and processed as described below for analysis of CD8 T cell responses. Where indicated, spleens were harvested 7 days after the last immunization for analysis of CD8 T cell responses.

Example 4

Intracellular Cytokine Staining (ICCS)

Immunized animals were bled from the tail vein and 100-120 μl of blood per mouse were resuspended in 2 ml of PBS (pH 7.4) containing 4% fetal calf serum (FCS), 2 mM ethylenediaminetetraacetic acid (EDTA) and 2.5 U/ml heparin. Blood samples were split into three aliquots and red blood cells were lysed using Red Blood Cell Lysing Buffer (Sigma-Aldrich, Steinheim, Germany). Peripheral blood mononuclear cells (PBMC) were finally resuspended in 2 ml of RPMI/10% FCS containing and 0.05 mM β-mercaptoethanol, 1 μl/ml GolgiPlug™ (BD Biosciences) blocking secretion of cytokines via the exocytotic pathway, and 1 μg/ml of peptides $OVA_{257-268}$ SIINFEKL (SEQ ID NO:3; "OVA"), $B8R_{20-27}$ TSYKFESV (SEQ ID NO:4; "B8R"), or no peptide ("no pept."). Peptides were purchased from ProImmune (Oxford, UK). CD8 T cell frequencies for the immunodominant $H-2K^b$-restricted TSYKFESV epitope derived from amino acids 20-27 of the viral B8R early protein (Tscharke, D. C., G. Karupiah, J. Zhou, T. Palmore, K. R. Irvine, S. M. Haeryfar, S. Williams, J. Sidney, A. Sette, J. R. Bennink, and J. W. Yewdell. 2005. Identification of poxvirus CD8+ T cell determinants to enable rational design and characterization of smallpox vaccines. J. Exp. Med. 201:95-104) were determined as a representative measure of vector-specific CD8 T cell responses. PBMC were incubated for 5 h at 37° C. in 5% $CO_2$, harvested by centrifugation, resuspended in 3 ml cold PBS/10% FCS/2 mM EDTA pH 7.4 and stored overnight at 4° C. The following day, PBMC were stained with antibodies anti-CD8α-Pac-Blue, anti-CD4-PerCP-Cy5.5, anti-CD62L-PE-Cy7, and in some experiments with anti-CD127-APC (all antibodies from BD Biosciences). PBMC were incubated with appropriate dilutions of the indicated antibodies for 30 min at 4° C. in the dark. After washing, cells were fixed and permeabilized by using the Cytofix/Cytoperm™ Plus kit (BD Biosciences) according to the manufacturer's instructions. After washing, PBMC were stained for intracellular interferon-γ (IFN-γ) and tumor necrosis factor-α (TNF-α) using a FITC-conjugated anti-IFN-γ antibody and PE-conjugated anti-TNF-α antibody (BD Biosciences). The antibodies were diluted in perm/wash buffer (BD Biosciences) and the PBMC were stained for 20 min at 4° C. in the dark. After washing, stained cells were analysed by flow cytometry on a BD Biosciences LSR II system.

Example 5

MHC Class I Pentamer and Dextramer Staining

Immunized animals were bled from the tail vein and 100-120 μl of blood per mouse were resuspended in 2 ml of PBS (pH 7.4) containing 4% fetal calf serum (FCS), 2 mM ethylenediaminetetraacetic acid (EDTA) and 2.5 U/ml heparin. Either the whole sample or an aliquot not used for ICCS were immediately subjected to staining of OVA- and B8R-specific CD8 T cells by anti-CD8α-Pac-Blue and either MHC class I pentamers (ProImmune) or by MHC class I dextramers (Immudex, Copenhagen, Denmark) complexed with the respective $H-2D^b$ binding peptides SIINFEKL and TSYKFESV. OVA and B8R-specific MHC class I pentamers were both labelled with APC and the respective CD8 T cell populations were stained in two separate reactions. MHC class I dextramers were labelled with either PE (SIINFEKL-dextramer) or APC (TSYKFESV-dextramer) and were combined in the one staining reaction together with anti-CD8α-Pac-Blue. After washing, stained cells were analysed by flow cytometry on a BD Biosciences LSR II system.

Example 6

ELISA for Detection of MVA-Specific Antibodies in Mouse Serum 96 well-plates were coated with crude extract of MVA-BN® infected CEF cells. Twofold serial dilutions of serum were incubated for 1 hour at RT. If necessary, pre-dilutions of mouse sera were prepared. For detection, the plates were incubated with a sheep-anti-mouse IgG-HRP detection antibody (Serotec) for 1 h at RT. TMB (Sigma-Aldrich) was used as substrate and the reaction was stopped by adding 1M $H_2SO_4$ (Merck). OD was measured at 450 nm with a Tecan F039300 Sunrise Absorbance Reader (Maennedorf, Switzerland).

Example 7

ELISA for Detection of OVA-Specific Antibodies in Mouse Serum 96 well-plates were coated with 0.25 μg/well chicken ovalbumin (Sigma-Aldrich). Twofold serial dilutions of serum were incubated overnight at 4° C. If necessary, pre-dilutions of mouse sera were prepared. Biotinylated Donkey-anti-mouse IgG H+L antibody (Dianova) was added to the plates for 2 hours at room temperature. For the detection of biotinylated secondary antibody, Streptavidine-HRP (Amersham Biosciences) was added to the plates and incubated for 2 hours at room temperature. ABTS (Sigma-Aldrich)/0.03% $H_2O_2$/0.1M citric acid was used to develop the assay. OD was measured at 405 nm, reference wave length 492 nm, with a Tecan F039300 Sunrise Absorbance Reader.

Example 8

Expression of eGFP Directed by Recombinant MVAs

Expression of eGFP in untreated HeLa cells, which are non-permissive for MVA was similar with all three promoters (FIG. 2A). In untreated CEF cells, which are permissive for MVA, the pS and the p7.5 promoters directed higher total eGFP expression than the pHyb promoter (FIG. 2B). To analyze early gene expression separately, the MVA infection cycle was arrested in its early phase by treatment with AraC for 16 h. Under these conditions, the pHyb promoter directed much higher eGFP expression than the pS and the p7.5 promoters (FIGS. 2A, B). In fact, the levels of eGFP in MVA-pHyb-eGFP-infected cells were not influenced by AraC. This showed that the tandem arrangement of the five early elements in pHyb (FIG. 1) was responsible for the observed increase in early antigen expression.

A kinetic analysis of eGFP expression in HeLa cells showed that the pHyb promoter directed protein expression within the first 30 min of infection, whereas significant eGFP expression from the pS promoter did not become detectable before 90 min (FIG. 2C). Moreover, the pHyb promoter directed higher levels of eGFP expression throughout the first 6 hours of infection (FIG. 2C). The expression levels from the p7.5 and the pS promoter reached those induced by the pHyb promoter only late in infection after more than 6 hours. Hence, at all time points between 0.5 and 6 h after infection, expression of eGFP with the pHyb promoter was significantly higher than that achieved with the p7.5 and the pS promoter. Equally important, the pHyb promoter activity was detectable very early within 30 min of infection, whereas p7.5 and pS required three times longer to induce detectable eGFP expression.

MHC class I (MHC I) presentation of the antigenic SIINFEKL peptide derived from OVA was analyzed after infection with MVA-pHyb-OVA, MVA-pS-OVA, or MVA-p7.5-OVA. The monoclonal antibody (mAb 25D1.16) specifically recognizes the complex of the SIINFEKL peptide bound the presenting MHC 1 molecule H-2 Kb. This antibody was used to detect SIINFEKL/MHC I complexes on the surface of murine EL4 T lymphoma cells. The kinetics of peptide presentation via MHC 1 molecules were largely dependent on the promoter chosen for antigen expression (FIG. 2D). After 90 min of infection a substantial amount of H2-Kb/SIINFEKL complexes was detectable on the surface of EL4 cells infected with MVA-pHyb-OVA indicating that OVA-derived CD8 T cell antigen was already presented at this early time point using the pHyb promoter. In contrast, even after 120 min of infection only minimal amounts of SIINFEKL were presented on the surface of MVA-pS-OVA or MVA-p7.5-OVA-infected cells (FIG. 2D). Throughout all time points of analysis, the presentation of the OVA peptide SIINFEKL was most efficient on cells infected with recombinant MVA-BN® expressing OVA under control of the pHyb promoter. At 24 h after infection, all cells in the culture presented SIINFEKL on MHC class I. This finding confirmed that all cells had initially been infected since MVA-BN® cannot spread in mouse cells and thus cannot infect new cells in a second cycle of infection. Therefore, the initial lack of SIINFEKL peptide presentation by EL4 cells inoculated with MVA-p7.5-OVA and MVA-pS-OVA was not due to a lower infection rate of the cells but due to lower presentation efficiency. Thus, the pHyb promoter was able to drive superior presentation of the antigen via MHC I to CD8 T cells compared to other promoters.

Example 9

Analysis of CD8 T Cell Responses

Figure 3:
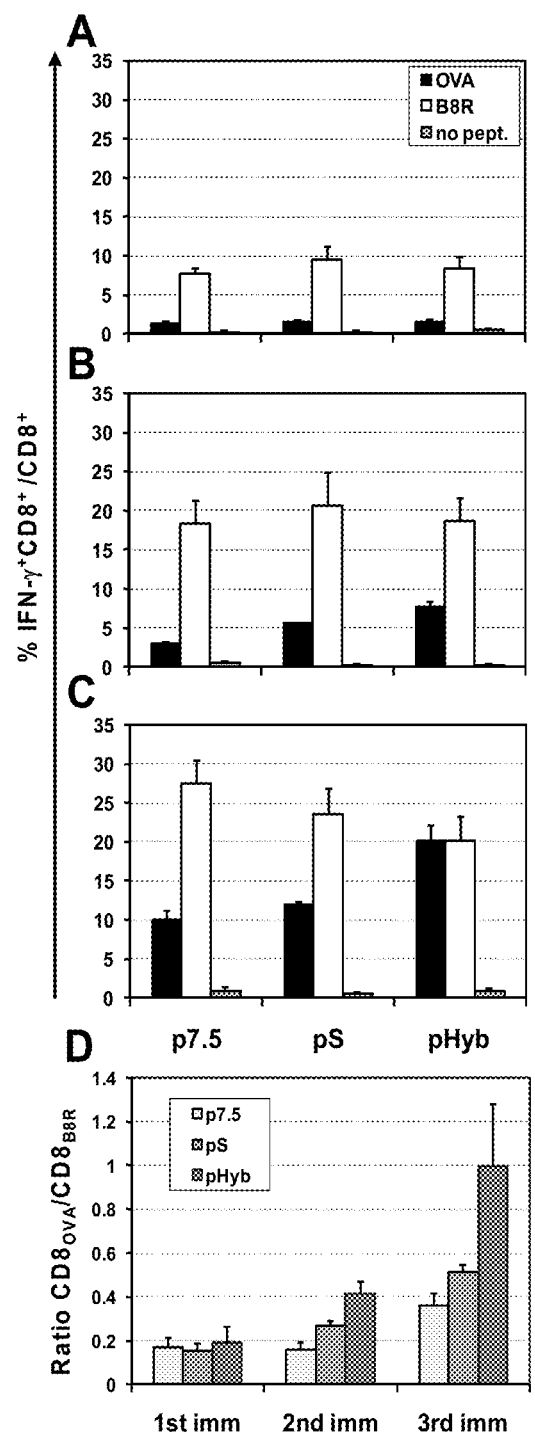
FIGS. 3 A-D depict analysis of chicken ovalbumin (OVA)- and MVA-specific CD8 T cell responses induced by recombinant MVAs. MVA-p7.5-OVA, MVA-pS-OVA ("pS"), and MVA-pHyb-OVA ("pHyb") were used to immunize groups of 5-6 BALB/c mice intraperitoneally (i.p.) at a dose of 108 TCID50 per mouse (A). Mice were boosted with a second (B), and third (C) i.p. injection 4 and 8 weeks after the first immunization, respectively. Leucocytes from blood were analyzed 6-8 days after the 1st and 6 days after 2nd and 3rd immunization for induction of OVA-specific ("OVA") and vector-specific ("B8R") CD8 T cell responses. Quantitation of antigen-specific CD8 T cells was done by intracellular cytokine staining for IFN-γ after a 6 h restimulation period and gating on CD4– CD8+ or CD19– CD8+ lymphocytes. Leucocytes from immunized animals incubated without peptide served as controls ("no pept."). Indicated are the percentages of OVA- and B8R-specific cells among total CD8 T cells (A-C). The percentages of OVA-(CD80VA) and B8R-specific (CD8B8R) CD8 T cells were used to calculate the ratios of CD80VA to CD8B8R cells (D). The log 10 of the ratios was used to calculate the standard error and Student's t-test. Shown are the combined results of two independent experiments (A-D).

CD8 T cell responses against recombinantly expressed OVA under the control of the promoters p7.5, pS and pHyb were determined in C57BL/6 mice after one, two, three, and four immunizations with $10^8$ TCID$_{50}$ of recombinant MVA per mouse. The OVA-specific CD8 T cell response was determined by ICCS for IFN-γ after stimulation with the K$^b$-restricted OVA-derived peptide SIINFEKL. To monitor the CD8 T cell response to the MVA vector, CD8 T cells recognizing the immunodominant CD8 T cell epitope from the poxviral B8R early protein were quantified by ICCS. One week after the first immunization, similar proportions of OVA-specific CD8 T cells were observed independent of the type of promoter used (FIG. 3A). The slightly higher numbers of OVA-specific CD8 T cells observed after the second immunization with MVA-pHyb-OVA compared to MVA-pS-OVA and MVA p7.5-OVA (FIG. 3B) were not statistically significant (p=0.27 and 0.62, respectively). B8R-specific CD8 T cell responses did also not differ significantly after the first and second immunization (p>0.5, FIG. 3A, B).

After the third immunization with MVA-pHyb-OVA, significantly stronger OVA-specific CD8 T cell responses were observed compared to triple immunization with MVA-pS-OVA (p<0.01) and with MVA-p7.5-OVA (p<0.001) (FIG. 3C). In contrast, there were no significant differences in the proportions of B8R-specific CD8 T cells of mice immunized with MVA-pHyb-OVA compared to mice treated with the two other MVA constructs (p>0.19).

Of note, these results demonstrate that it was possible to significantly increase the number of OVA-specific CD8 T cells even after two previous immunizations with the homologous MVA virus construct. The ability of the MVA vector to boost antigen-specific CD8 T cell responses was independent of the promoter (p<0.001 for OVA-specific CD8 T cells after 3 vs. 2 homologous immunizations with each of the three recombinant MVA constructs). The proportion of OVA-specific CD8 T cells reached exceptionally high numbers after three immunizations with MVA-pHyb-OVA. Up to 20% of all CD8 T cells were OVA-specific 6 days after the third immunization with this construct (FIG. 3C). Almost equal proportions of OVA-specific CD8 T cells compared to B8R-specific CD8 T cells were detected at day 6 after the third immunization with MVA-pHyb-OVA using ICCS (FIG. 3C). This was partly due to the decrease in relative numbers of B8R-specific CD8 T cells, suggesting that expansion of primed OVA-specific CD8 T cells was stimulated with higher efficiency (FIG. 3C). The ratio of OVA-specific to B8R-specific CD8 T cells was significantly different after 3 immunizations with MVA-pHyb-OVA compared to the two other promoters (FIG. 3D). In contrast, this ratio was very similar for all three constructs after the first immunization. The enhancing effect of pHyb was becoming apparent after 2 immunizations but was not statistically significant at this time point (FIG. 3D). Taken together, the $CD8_{OVA}:CD8_{B8R}$ ratios indicate that the pHyb promoter exerts its advantage in booster immunizations and particularly after the second boost. Notably, the $CD8_{OVA}:CD8_{B8R}$ ratios also suggest that the pS promoter was indeed less efficient than the pHyb promoter but had an advantage over the p7.5 promoter (FIG. 3D).

Figure 4:
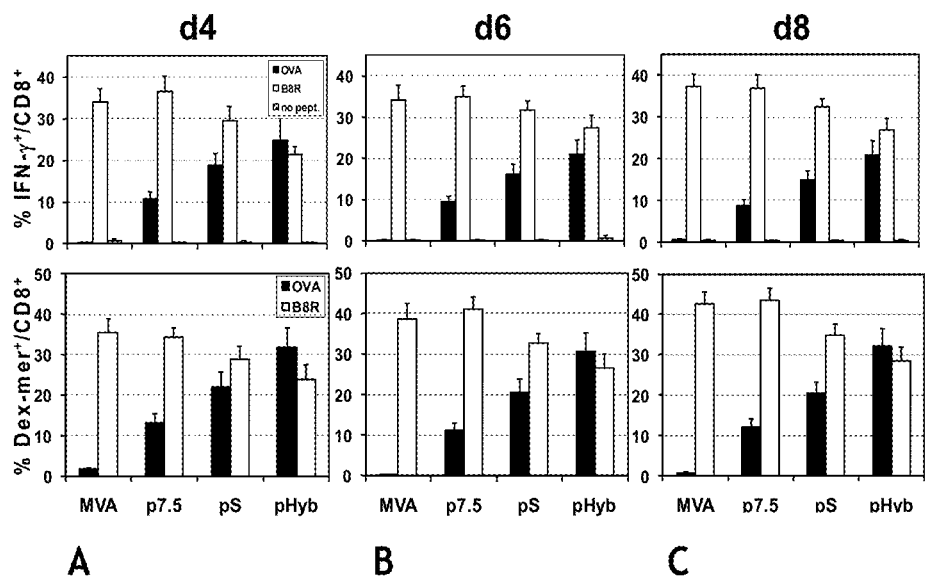
FIGS. 4 A-C depict kinetics of OVA- and MVA-specific CD8 T cell responses after three immunizations with recombinant MVAs. MVA-p7.5-OVA, MVA-pS-OVA ("pS"), MVA-pHyb-OVA ("pHyb") were used to immunize groups of 5-6 BALB/c mice intraperitoneally (i.p.) at a dose of 108 TCID50 per mouse (A). Mice were boosted with a second (B), and third (C) i.p. injection 4 and 8 weeks after the first immunization, respectively. Leucocytes from blood were analyzed 4, 6, and 8 days after the 3rd immunization for induction of OVA-specific ("OVA") and vector-specific ("B8R") CD8 T cell responses. Quantitation of antigen-specific CD8 T cells was done by intracellular cytokine staining for IFN-γ after a 6 h restimulation period and gating on CD19– CD8+ lymphocytes (upper panels) or by MHC class I dextramer staining (lower panels). Leucocytes from immunized animals incubated without peptide served as controls ("no pept."). Indicated are the percentages of OVA- and B8R-specific cells among total CD8 T cells.

When OVA-specific CD8 T cell responses were analyzed at different time points after the third immunization, it was found that OVA-specific CD8 T cells were immunodominant at specific time points after the boost as determined by ICCS (FIG. 4). Reversal of immunodominance was observed at 4 or 6 days after the third immunization depending on the experiment (FIG. 4 and data not shown). In some experiments, four immunizations with MVA-pHyb-OVA were required to achieve a ratio of OVA to B8R-specific CD8 T cells of >1 (data not shown). By contrast, after three or four immunizations with MVA-pS-OVA, B8R-specific CD8 T cells always remained immunodominant (FIG. 4 and data not shown). These results were confirmed by employing the MHC class I Dextramer™ staining method, a modification of the well described MHC class I tetramer staining technique. Using this approach, higher OVA-specific than B8R-specific CD8 T cells were observed at all time points after the third immunization with MVA-pHyb-OVA, but never with the p7.5 or pS promoter (FIG. 4). Thus, only the pHyb promoter was able to reverse CD8 T cell immunodominance in favor of the pHyb-driven antigen.

Example 10

CD8 T Cell Memory

Figure 5:
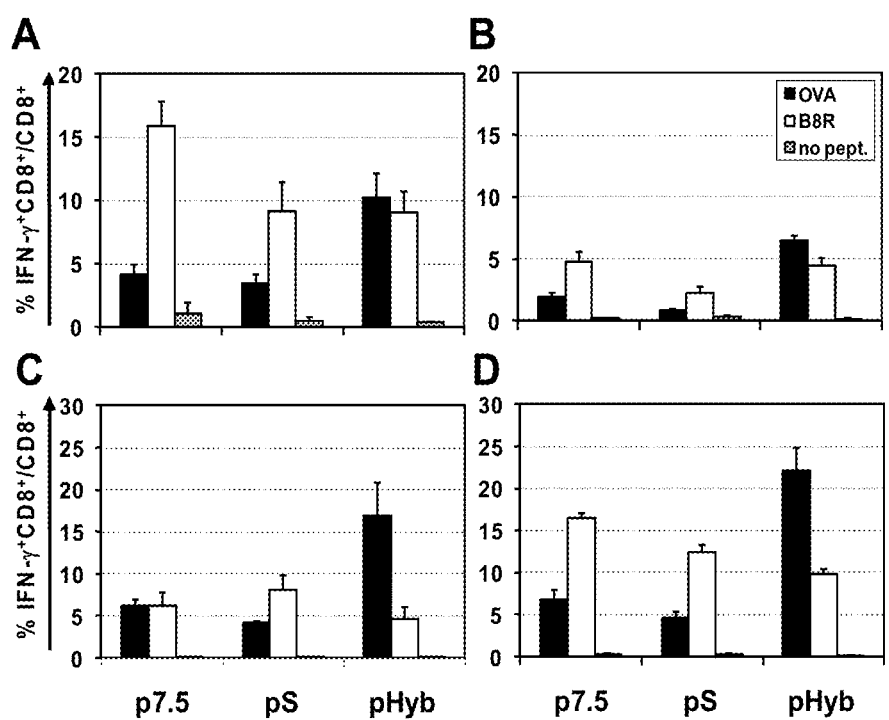
FIGS. 5 A-D depict OVA- and MVA-specific memory CD8 T cells. Leucocytes from BALB/c mice immunized with MVA-p7.5-OVA, MVA-pS-OVA, and MVA-pHyb-OVA were prepared and analyzed 28 days (A) and 92 days (B) after the third immunization by ICCS for IFN-γ to quantify OVA and B8R-specific CD8 T cells. Animals were from one of the two experiments shown in FIG. 3. Three of the five mice immunized three times with MVA-pHyb-OVA and five mice immunized three times with MVA-p7.5-OVA and MVA-pS-OVA were vaccinated a fourth time with the respective OVA-expressing MVA recombinants 14 weeks after the third immunization. Mice were analyzed by IFN-γ-ICCS for OVA- and B8R-specific CD8 T cells in blood (C) and spleen (D) 6 days after the booster immunization. Leucocytes from the immunized animals incubated without peptide served as controls ("no pept.").

In the early memory phase, at 28 days after the third immunization with MVA-pHyb, OVA-specific CD8 T cells still outnumbered B8R-specific CD8 T cells and were significantly higher compared to mice immunized three times with MVA-pS-OVA (FIG. 5A, p=0.0035). Analysis of long-term CD8 T cell memory in blood of mice 13 weeks after the third immunization demonstrated that OVA-specific CD8 T cells were still significantly higher for MVA-pHyb-OVA compared to MVA-pS-OVA (FIG. 5B, p<0.001 using Student's t-test) and MVA-p7.5-OVA (p=0.03). This result was confirmed by staining with MHC class I pentamers detecting B8R- and OVA-specific CD8 T cells (data not shown). Irrespective of the type of promoter, approximately 70-80% of all OVA-specific CD8 T cells detected by MHC class I pentamer staining were of the effector memory phenotype (CD62L$^-$/CD127$^+$) at 12 weeks after the third immunization (data not shown). In conclusion, pHyb was able to induce a strong and long-lasting CD8 T cell response against the antigen and the proportions of OVA- and B8R-specific cells found in the early phase after the third immunization with the three MVA constructs were essentially preserved in the memory phase.

Example 11

Effect of Four Immunizations

Fourteen weeks after the third immunization mice were again boosted with the same MVA constructs to determine whether the proportions of OVA-specific CD8 T cells in the blood of MVA-pS-OVA or MVA-p7.5-OVA immunized mice would catch up and reach similar levels like those of MVA-pHyb-OVA immunized animals. However, MVA-pHyb-OVA was again most efficient and induced the highest number of OVA-specific CD8 T cells in blood (FIG. 5C). In contrast to pHyb, pS and p7.5 were not able to shift the immunodominance pattern in favour of OVA-specific CD8 T cells even after four immunizations. Analysis of splenocytes from the same mice showed a very similar ratio of OVA-specific to B8R-specific CD8 T cells compared to the ratios of the two CD8 T cell specificities in blood (FIG. 5C, D) indicating that the relative numbers of OVA and B8R-specific CD8 T cells obtained by analysis of peripheral blood were representative for the whole CD8 T cell compartment.

The invention claimed is:

1. A vaccinia virus vector comprising a promoter comprising at least two nucleotide sequence elements, each having nucleotides 48-81 of SEQ ID NO:1.

2. A recombinant modified vaccinia virus Ankara (MVA) comprising a promoter comprising at least two nucleotide sequence elements, each having nucleotides 48-81 of SEQ ID NO:1.

3. The vaccinia virus vector of claim 1, comprising at least five nucleotide sequence elements, each having nucleotides 48-81 of SEQ ID NO:1.

4. The MVA vector of claim 2, comprising at least five nucleotide sequence elements, each having nucleotides 48-81 of SEQ ID NO:1.

5. The vaccinia virus vector of claim 1, further comprising at least one late promoter element.

6. The MVA vector of claim 2, further comprising at least one late promoter element.

7. The vaccinia virus vector of claim 1, further comprising at least one cowpox ATI late promoter element.

8. The MVA vector of claim 2, further comprising at least one cowpox ATI late promoter element.

9. The vaccinia virus viral vector of claim 1, further comprising nucleotides 1-14 of SEQ ID NO:1.

10. The MVA vector of claim 2, further comprising nucleotides 1-14 of SEQ ID NO:1.

11. The MVA vector of claim 4, further comprising nucleotides 1-14 of SEQ ID NO:1.

* * * * *

SEQUENCE LISTING

```
<160> NUMBER OF SEQ ID NOS: 5

<210> SEQ ID NO 1
<211> LENGTH: 247
<212> TYPE: DNA
<213> ORGANISM: Artificial Sequence
<220> FEATURE:
<223> OTHER INFORMATION: Optimized 1xL/5xE Promoter

<400> SEQUENCE: 1
acgcgtgttt aaacgttttg aaaatttttt tataataaat atccggtaaa aattgaaaaa      60
ctattctaat ttattgcacg gtccggtaaa aattgaaaaa ctattctaat ttattgcacg     120
gtccggtaaa aattgaaaaa ctattctaat ttattgcacg gtccggtaaa aattgaaaaa     180
ctattctaat ttattgcacg gtccggtaaa aattgaaaaa ctattctaat ttattgcacg     240
gtccgga                                                              247

<210> SEQ ID NO 2
<211> LENGTH: 40
<212> TYPE: DNA
<213> ORGANISM: Artificial Sequence
<220> FEATURE:
<223> OTHER INFORMATION: Synthetic pS promoter

<400> SEQUENCE: 2
aaaaattgaa attttatttt ttttttttgg aatataaata                           40

<210> SEQ ID NO 3
<211> LENGTH: 8
<212> TYPE: PRT
<213> ORGANISM: Artificial Sequence
<220> FEATURE:
<223> OTHER INFORMATION: Kb-restricted OVA-derived peptide

<400> SEQUENCE: 3
```

```
Ser Ile Ile Asn Phe Glu Lys Leu
1               5

<210> SEQ ID NO 4
<211> LENGTH: 8
<212> TYPE: PRT
<213> ORGANISM: Vaccinia virus

<400> SEQUENCE: 4

Thr Ser Tyr Lys Phe Glu Ser Val
1               5

<210> SEQ ID NO 5
<211> LENGTH: 34
<212> TYPE: DNA
<213> ORGANISM: Vaccinia virus

<400> SEQUENCE: 5
aaaaattgaa aaactagtct aatttattgc acgg                              34
```